US012527901B2

(12) United States Patent
Shashanka Jain

(10) Patent No.: US 12,527,901 B2
(45) Date of Patent: Jan. 20, 2026

(54) AUTOMATED PERITONEAL DIALYSIS USING BELLOWS

(71) Applicants: BAXTER INTERNATIONAL INC., Deerfield, IL (US); BAXTER HEALTHCARE SA, Glattpark (CH)

(72) Inventor: Belur Shanthakumar Shashanka Jain, Bangalore (IN)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 507 days.

(21) Appl. No.: 18/008,270

(22) PCT Filed: Jun. 3, 2021

(86) PCT No.: PCT/US2021/035721

§ 371 (c)(1),
(2) Date: Dec. 5, 2022

(87) PCT Pub. No.: WO2021/247877

PCT Pub. Date: Dec. 9, 2021

(65) Prior Publication Data

US 2023/0285649 A1 Sep. 14, 2023

(30) Foreign Application Priority Data

Jun. 5, 2020 (IN) ............................ 202041023707

(51) Int. Cl.
*A61M 1/28* (2006.01)
*A61M 1/14* (2006.01)

(52) U.S. Cl.
CPC ............ *A61M 1/282* (2014.02); *A61M 1/154* (2022.05); *A61M 1/155* (2022.05); (Continued)

(58) Field of Classification Search
CPC ...... A61M 1/154; A61M 1/155; A61M 1/156; A61M 1/1562; A61M 1/1565; A61M 1/159; A61M 1/282; A61M 2205/3331
See application file for complete search history.

(56) References Cited

U.S. PATENT DOCUMENTS

| | | | |
|---|---|---|---|
| 2019/0321535 A1 | 10/2019 | Beavers et al. |
| 2021/0138139 A1 | 5/2021 | Hedmann et al. |

FOREIGN PATENT DOCUMENTS

| | | |
|---|---|---|
| EP | 0157024 | 10/1985 |
| WO | 2006054720 | 5/2006 |
| WO | 2019007992 | 1/2019 |

OTHER PUBLICATIONS

English translation WO 2006054720 A1 (2006).*

(Continued)

*Primary Examiner* — John Kim
(74) *Attorney, Agent, or Firm* — K&L Gates LLP

(57) ABSTRACT

A peritoneal dialysis system includes: a bellows; a common inlet/outlet fluid receptacle in fluid communication with the bellows; a plurality of fluid lines in fluid communication with the common inlet/outlet line; a linear actuator positioned and arranged to expand and compress the bellows; a plurality of valves positioned and arranged to allow or occlude flow through the plurality of fluid lines to or from the bellows; and a control unit configured to control the linear actuator and the plurality of valves.

24 Claims, 17 Drawing Sheets

(52) U.S. Cl.
CPC .......... *A61M 1/1562* (2022.05); *A61M 1/159* (2022.05); *A61M 1/156* (2022.05); *A61M 1/1565* (2022.05); *A61M 2205/3331* (2013.01)

(56) References Cited

OTHER PUBLICATIONS

International Preliminary Report on Patentability and Written Opinion for International application No. PCT/US2021/035721 dated Dec. 15, 2022.
International Search Report—International Application No. PCT/US2021/035721 mailing date Nov. 11, 2021—14 pages.
Written Opinion—International Application No. PCT/US2021/035721 mailing date Nov. 11, 2021—12 pages.

* cited by examiner

AUTOMATED PERITONEAL DIALYSIS USING BELLOWS

PRIORITY CLAIM

This application is a national phase entry of PCT Application No. PCT/US2021/035721, filed on Jun. 3, 2021, which claims priority to and the benefit of Indian provisional application No. 202041023707, filed on Jun. 5, 2020, the entire disclosures of which are incorporated herein by reference and relied upon in their entirety.

BACKGROUND

The present disclosure relates generally to medical fluid treatments and in particular to dialysis fluid treatments.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal chamber. APD machines also allow for the dialysis fluid to dwell within the chamber and for the transfer of waste, toxins and excess water to take place. The source may include multiple liters of dialysis fluid including several solution bags.

APD machines pump used or spent dialysate from the peritoneal chamber, though the catheter, and to the drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

In any of the above modalities using an automated machine, the automated machine operates typically with a disposable set, which is discarded after a single use. Depending upon the complexity of the disposable set, the cost of using one set per day may become significant. Also, daily disposables require space for storage, which can become a nuisance for home owners and businesses. Moreover, daily disposable replacement requires daily setup time and effort by the patient or caregiver at home or at a clinic.

There is also a need for APD devices to be portable so that a patient may bring his or her device on vacation or for work travel.

For each of the above reasons, it is desirable to provide a relatively simple, compact APD machine, which operates a simple and cost effective disposable set.

SUMMARY

The present disclosure relates to an automated peritoneal dialysis ("APD") system, which uses a bellows pump. In general, the APD system employs an APD machine or cycler that operates a disposable set. In one embodiment, the disposable set includes at least one bellows, which is expanded to perform a draw or fill stroke and is compressed to perform an expel or pump-out stroke. The bellows connects to a common input/output line that feeds fluid into the bellows and accepts fluid from the bellows. The common input/output line feeds or splits into multiple, e.g., five, separate lines, each interfacing with a valve, such as an electrically actuated solenoid valve, a motorized pinch valve, or a pneumatically actuated valve. The separate lines include a fresh dialysis fluid line that extends to a fresh dialysis fluid supply or bag, a last fill fluid line that extends to a last dialysis fluid supply or bag, a patient line that carries fresh, heated dialysis to a patient and used dialysis fluid from the patient, a drain line that extends to a drain container, e.g., bag, or to a house drain such as a toilet or bathtub, and a heater line that carries fresh dialysis fluid to a heater disposable, such as a container or bag having serpentine heating pathway.

The bellows in an embodiment has an accordion or concertina shape and may be made of a disposable plastic, such as polyvinyl chloride ("PVC"), polyethylene ("PE"), polyurethane ("PU"), polypropylene ("PP"), polycarbonate or other generally soft plastic material. One possible bellows driving structure includes a motor that rotates a shaft to which a gear is connected, in which the gear forms the pinion of a rack and pinion type of linear actuator. The rotational motion of the motor shaft is converted into translational motion by the rack and pinion. The translational motion of the rack and pinion causes expansion and compression of the bellows depending on the direction of motor rotation. A slide potentiometer may be provided to monitor the positon and movement of the bellows. Alternatively, the motor is fitted with a motor encoder, which detects the rotational position of the motor shaft, which can be converted into a distance moved by the rack and pinion and thus the bellows by knowing how much the rack moves per rotation, or partial rotation, of the motor shaft and pinion gear.

Other forms of linear actuation may be used, such as a motor and lead or ball screw, a linear motor or a pneumatic cylinder. Each linear actuator is able to expand and compress the bellows.

Volumetric accuracy for the APD system is determined in one embodiment by knowing the internal volume of the bellows and by detecting how much the bellows has been moved. Volumetric accuracy also assumes the bellows to be completely full of fluid and thus fully primed with air. If needed, the bellows may be fitted with one or more hydrophobic membrane to help "squeeze" the air out of the bellows during operation. A priming sequence for the bellows APD system is described below.

It is contemplated to include a set of two bellows that are operated in an alternating manner to provide a more continuous flow and to increase flowrate. In an embodiment, the linear actuator, e.g., motor operably coupled to a rack and pinion, is connected to the bellows at a location at which the two bellows are connected together, so that the linear actuator in (i) a first stroke moves in a first direction to expand a first bellows to draw fluid in and compress the second bellows to pump fluid out and (ii) a second stroke moves in a second direction to expand the second bellows to draw fluid in and compress first bellows to pump fluid out. The result is a more continuous flow and an increased flowrate using the same linear actuator as for the single bellows embodiment. The trade-off is (i) the additional disposable cost of the second bellows and a second set of lines to each of the sources and destinations and (ii) the additional cost and complexity of a second set of valves and their control of the second set of lines.

As mentioned above, it is important to prime the bellows APD system for volumetric accuracy and to prevent the delivery of air to the patient. It is contemplated to allow the bellows to be tipped during priming either in a motorized way or manually, so that air migrates towards the inlet/outlet of the bellows for removal to the drain line. Alternatively or additionally, the bellows may be fitted with one or more hydrophobic membrane that aids air in escaping the bellows during priming.

Further alternatively or additionally, in one priming sequence under control of the control unit of the present APD system, the single or dual bellows pump is caused to first prime the supply line. If the volume of a single stroke of the bellows pump is less than that of the supply line, then it is contemplated to open the supply line valve on the draw stroke of the bellows pump, and then to close that valve and open the drain valve to push air in the subsequent pump-out stroke of the bellows to drain. The above sequence is repeated until the supply line is fully primed, which may be detected by a sensor located at the common input/output line, or determined empirically to require a certain amount of pump strokes.

The priming operation of the supply line is then repeated for all supply lines and the last bag line. With the supply and last bag lines primed, fresh dialysis fluid is then used to prime the patient line up to a patient connector, which may be set at a certain height or the patient connector may be placed next to a sensor that determines when the patient line is fully primed. The heater line is then primed at least up to its interaction with a heater valve. The drain line may or may not be primed, e.g., may be primed up to a drain line valve.

The single or dual bellows APD system of the present disclosure contemplates different solutions for ensuring that the motorized bellows does not create too much positive or negative fluid pumping pressure when delivering fresh dialysis to or removing used dialysis fluid from the patient. Generally, it is desirable to limit patient pumping pressure for peritoneal dialysis to −1.5 psig for effluent removal and from +1.5 psig to 3.0 psig for fresh dialysis fluid delivery to the patient. Pumping from other sources or to other destinations may be performed at higher pressures.

A first pressure control solution is to select a motor that is incapable of supplying (or is controlled not to supply) a positive or negative overpressure. The pressure that fluid is delivered to and removed from the patient is a function of the force exerted by the linear actuator and the geometry of the bellows and tubing. The maximum positive and negative patient pumping pressures are known (listed above) as is the geometry of the bellows and tubing. From these values, the maximum allowable force due to the linear actuator is able to be calculated. Discussed herein is the determination of a relationship between output force of the linear actuator, e.g., the rack and pinion configuration and the motor torque outputted by the motor. Thus after calculating the maximum allowable force due to the linear actuator, the maximum allowable motor torque may be calculated. A single speed motor having a set torque at or below the maximum is then selected. Or, a variable speed motor is selected and a low speed limit is set for patient pumping (motor torque has an inverse relationship with motor speed). A control unit of the APD system of the present disclosure either causes the single speed motor to be powered or maintains the low speed limit for the variable speed motor for patient pumping (limit may not apply for pumping to or from other destinations or sources).

A second pressure control solution contemplated for the bellows APD system of the present disclosure is to place a force sensor (load cell or strain gauge) in contact with the bellows. Here, instead of calculating a maximum allowable motor torque for patient pumping, the actual force due to the linear actuator is measured. The measurement may be used as feedback to the control unit of APD system, which causes the speed of the motor to be varied to ensure that the resulting force due to the linear actuator is at or below the maximum allowable force. The maximum allowable force due to the linear actuator is calculated again knowing the maximum allowable positive and negative patient pumping pressures and the geometry of the bellows and tubing. To reduce noise leading to error, such as force to torque conversion, current to torque conversion and current sensing error, it is contemplated to locate the force sensor close the item to be sensed, namely, the bellows. Doing so reduces or eliminates these errors.

A third pressure control solution contemplated for the bellows APD system of the present disclosure is to add a pressure sensing module or pod that measures fluid pressure directly and obviates the need to know the bellows and tubing geometry and the need to determine maximum allowable forces. The pod may have a membrane that separates a fluid pumping side of the pod from an air transducer sensing side of the pod. The flexibility of the membrane allows the pressure on either side of the membrane to equilibrate, such that the pressure of any of the different fluids discussed herein equals the sensed air pressure. A pressure transducer is provided and measures the pressure of air or other transmission fluid, which equals that of the PD or patient fluid. The pressure signal is used as feedback to the control unit to vary the speed of the bellows motor to make sure that the resulting positive or negative fluid pressure does not exceed an allowable limit.

In an alternative embodiment, the pressure "pod" is made to be very small, e.g., to be a dome that covers a pressure sensing area or diaphragm located along a tube. The dome and diaphragm may be welded to the tube, e.g., via ultrasonic welding, heat sealing or solvent bonding, so that the dome and diaphragm cover a pressure sensing hole in the tube. The dome communicates pneumatically with a pressure transducer in the same manner described herein for the pressure pod embodiments.

It is contemplated to provide a diaphragm positioning apparatus and method that may be used with any of the pressure sensing embodiments of the bellows APD system of the present disclosure, including the direct tube pressure sensing embodiment. The positioning apparatus includes the pod or dome and its associated diaphragm, the pressure transducer and an additional vent valve. During a time in which the cycler is not pumping fluid, the diaphragm is pressurized with a liquid so as to be located at a starting position. The cycler then attempts to pump over a full range of positive and negative pressures to see if the starting position of the diaphragm allows for a pressure to be sensed over the full desired pressure range. If so, then that initial diaphragm starting position is noted and used going forward. If not, and the diaphragm during the test instead reaches a positive or negative elastic limit and no longer senses properly in that positive or negative direction, the cycler opens the vent and starts over. Upon the start over, the cycler places the diaphragm at a new starting position that attempts to correct against the direction in which the prior positive or negative failure occurred. If an elastic limit is reached again, the vent valve is reopened and the above process is repeated until a suitable starting location for the diaphragm is found.

For any of the pressure sensing versions of the bellows APD system of the present disclosure, it is contemplated to provide a calibration routine that determines the actual volumetric output of the bellows. Doing so allows for the manufacturing tolerances of the bellows to be relaxed, lowering disposable cost. For the calibration routine, the pneumatic transmission line extending from the pressure pod to the pressure transducer (and to the vent valve if provided for the pressure diaphragm starting location procedure) also extends to a known volume cylinder. A piston is located within the cylinder and is driven by a linear actuator, such as a rotating nut motor that turns a ball or lead screw. The linear actuator in one embodiment provides a piston rod for driving a piston head that is moveably sealed within the cylinder. A position sensing device, such as an encoder or potentiometer, is provided to accurately detect a position of the piston head within the cylinder.

In the calibration routine, the bellows is moved a known distance to displace fluid into the pressure pod. All downstream fluid valves are closed so pressure builds from an initial pressure to an increased pressure. Next, the piston is retracted within the cylinder so that the pneumatic pressure as measured by the pressure transducer is lowered from the increased pressure to the initial pressure. Because the initial and final pressures are equal, the volume as defined by the inner diameter cross-sectional area of the cylinder multiplied by the distance that the piston head is moved to reach the initial pressure equals the volume of fluid delivered from the bellows to the pressure pod. The control unit records the actual volume of dialysis fluid delivered over the first moved distance of the bellows.

With the bellows maintained at the first moved distance, at least a portion of the fluid in the pressure pod is removed to drain via the piston and cylinder. The above-described procedure is then repeated, moving the bellows from the first moved distance to a second moved distance. The control unit records the actual volume of dialysis fluid delivered by the bellows over the second moved distance. The first and second moved distances may be the same or different. When the bellows is finally moved a full stroke, the control unit adds all the incremental volumes to determine a total actual stroke volume for the bellows. The control unit thereafter has a map for the particular bellows that provides actual stroke volumes for partial and full strokes. It is contemplated to perform the calibration routine at the beginning of each treatment, so that a custom volume delivery profile can be developed for each bellows disposable set, allowing for wider tolerances in the production of the bellows.

In a further alternative bellows APD system of the present disclosure, pressure is still controlled directly but the pressure pods or domes are eliminated, which simplifies the disposable and lowers its cost. Here, an incompressible fluid column is located between the linear actuator and the bellows. The incompressible fluid column is located within a chamber and contacts a slidingly sealed piston, e.g., o-ring sealed to the chamber. The piston is coupled mechanically to the bellows. The linear actuator translates the chamber so that the incompressible fluid (e.g., water or oil) is compressed between the chamber and the piston. The incompressible fluid is in fluid communication with a liquid or fluid pressure transducer, which outputs to a control unit. The control unit uses the sensed pressure as feedback to control the actual pressure to meet a commanded pressure.

In an embodiment, the inner diameter of the incompressible fluid chamber (the outer diameter of the incompressible fluid column) is made to be the same as the effective pumping diameter of the bellows. In this way, the pressure applied by the linear actuator to the incompressible fluid is the same as the pressure applied by the bellows to the fresh or used PD fluid. Thus controlling the pressure of the incompressible fluid also controls the pressure of the dialysis fluid. In an alternative implementation, two or more incompressible fluid columns are provided, each sensed by a liquid or fluid pressure sensor, for redundancy and accuracy.

In light of the disclosure set forth herein, and without limiting the disclosure in any way, in a first aspect of the present disclosure, which may be combined with any other aspect or portion thereof, a peritoneal dialysis system includes: a bellows; a common inlet/outlet fluid receptacle in fluid communication with the bellows; a plurality of fluid lines in fluid communication with the common inlet/outlet receptacle; a linear actuator positioned and arranged to expand and compress the bellows; a plurality of valves positioned and arranged to allow or occlude flow through the plurality of fluid lines to or from the bellows; and a control unit configured to control the linear actuator and the plurality of valves.

In a second aspect of the present disclosure, which may be combined with any other aspect or portion thereof, the peritoneal dialysis system includes at least one means for limiting the pressure of fluid pulled into or pushed out of the bellows.

In a third aspect of the present disclosure, which may be combined with any other aspect or portion thereof, the plurality of fluid lines includes at least one of a fresh dialysis fluid line, a heater line, a patient line or a drain line.

In a fourth aspect of the present disclosure, which may be combined with any other aspect or portion thereof, the peritoneal dialysis system includes at least one of a fresh dialysis fluid container in fluid communication with the at least one fresh dialysis fluid line, a heating container in fluid communication with the heater line, or a drain container in fluid communication with the drain line.

In a fifth aspect of the present disclosure, which may be combined with any other aspect or portion thereof, the common inlet/outlet fluid receptacle includes a common inlet/outlet fluid line or a pressure pod.

In a sixth aspect of the present disclosure, which may be combined with any other aspect or portion thereof, the linear actuator includes a motor in operable communication with a rack and pinion, the rack positioned and arranged to expand and compress the bellows.

In a seventh aspect of the present disclosure, which may be combined with any other aspect or portion thereof, the peritoneal dialysis system includes a positional feedback device outputting to the control unit to enable the control unit to determine a current position of the bellows.

In an eighth aspect of the present disclosure, which may be combined with any other aspect or portion thereof, the positional feedback device of the seventh aspect includes a potentiometer or a motor encoder.

In a ninth aspect of the present disclosure, which may be combined with any other aspect or portion thereof, the control unit is configured to use the current position of the bellows to determine at least one of (i) a volume of fluid moved into or out of the bellows or (ii) a flowrate of fluid moved into or out of the bellows.

In a tenth aspect of the present disclosure, which may be combined with any other aspect or portion thereof, the control unit is configured to perform a priming sequence in which fluid is pulled through a first one of the fluid lines when the bellows is expanded and air is pushed out a second one of the fluid lines when the bellows is compressed.

In an eleventh aspect of the present disclosure, which may be combined with any other aspect or portion thereof, the bellows is a first bellows, and which includes a second bellows positioned and arranged such that the first bellows is expanded while the second bellows is compressed and the first bellows is compressed while the second bellows is expanded.

In a twelfth aspect of the present disclosure, which may be combined with any other aspect or portion thereof, the linear actuator is positioned and arranged to expand and compress the first and second bellows.

In a thirteenth aspect of the present disclosure, which may be combined with any other aspect or portion thereof, the common inlet/outlet receptacle is a first common inlet/outlet receptacle and which includes a second common inlet/outlet receptacle in fluid communication with the second bellows.

In a fourteenth aspect of the present disclosure, which may be combined with any other aspect or portion thereof, a peritoneal dialysis system includes: a bellows; a plurality of fluid lines in fluid communication with the bellows; a plurality of valves positioned and arranged to allow or occlude flow through the plurality of fluid lines to or from the bellows; a linear actuator positioned and arranged to expand and compress the bellows, the linear actuator including a motor; and a control unit configured to control the motor of the linear actuator and the plurality of valves, wherein (i) the motor is selected so as to be incapable of causing fluid moved by the linear actuator to exceed a pressure limit or (ii) the control unit is configured to control the motor to ensure that fluid moved by the linear actuator is within the pressure limit.

In a fifteenth aspect of the present disclosure, which may be combined with any other aspect or portion thereof, control of the linear actuator is based on a mathematical relationship involving the linear actuator and the motor.

In a sixteenth aspect of the present disclosure, which may be combined with any other aspect or portion thereof, a peritoneal dialysis system includes: a bellows; a linear actuator positioned and arranged to expand and compress the bellows; a force sensor in operable communication with the bellows and the linear actuator; and a control unit configured to control the linear actuator based on an output from the force sensor to ensure that fluid moved by the bellows is within a pressure limit.

In a seventeenth aspect of the present disclosure, which may be combined with any other aspect or portion thereof, control of the linear actuator is based on a maximum allowable force determined knowing the pressure limit and at least one geometrical dimension associated with the bellows.

In an eighteenth aspect of the present disclosure, which may be combined with any other aspect or portion thereof, the force sensor is located at a contact point between the bellows and the linear actuator.

In a nineteenth aspect of the present disclosure, which may be combined with any other aspect or portion thereof, a peritoneal dialysis system includes: a bellows; a linear actuator positioned and arranged to expand and compress the bellows; a pressure sensor in fluid communication with the bellows; and a control unit configured to control the linear actuator based on an output from the pressure sensor to ensure that fluid moved by the bellows is within a pressure limit.

In a twentieth aspect of the present disclosure, which may be combined with any other aspect or portion thereof, the pressure sensor includes a diaphragm separating a first side of the pressure sensor in fluid communication with the bellows from a second side in operable communication with a pressure transducer.

In a twenty-first aspect of the present disclosure, which may be combined with any other aspect or portion thereof, the control unit is further configured to (i) cause the diaphragm to be moved to a starting position, (ii) actuate the linear actuator to cause the bellows to pump over a full range of positive and negative pressures and determine if the diaphragm flexes over the full range, (iii) if the diaphragm flexes over the full range, use the starting position for the diaphragm for treatment, and (iv) if the diaphragm does not flex over the full range, repeat (i) to (iv) moving the diaphragm to a different starting position.

In a twenty-second aspect of the present disclosure, which may be combined with any other aspect or portion thereof, the diaphragm is part of a tube in fluid communication with the bellows.

In a twenty-third aspect of the present disclosure, which may be combined with any other aspect or portion thereof, a peritoneal dialysis system includes: a bellows; a piston in mechanical communication with the bellows; a chamber, the piston in moveably sealed communication with the chamber, the chamber and the piston holding an incompressible fluid; a pressure sensor in operable communication with the incompressible fluid; and a linear actuator positioned and arranged to move the chamber and the bellows; and a control unit configured to use feedback from the pressure sensor to attempt to control the linear actuator so that a pressure of a fluid delivered or removed by the bellows meets a commanded pressure.

In a twenty-fourth aspect of the present disclosure, which may be combined with any other aspect or portion thereof, the chamber holds a plurality of incompressible fluid columns in fluid communication with at least one pressure sensor.

In a twenty-fifth aspect of the present disclosure, which may be combined with any other aspect or portion thereof, a fluid system includes: a fluid pump including a fluid contacting portion and an actuating portion for actuating the fluid contacting portion; a pressure sensor including a diaphragm separating a first side of the pressure sensor in fluid communication with the fluid contacting portion of the fluid pump from a second side of the pressure sensor in operable communication with a pressure transducer; and a control unit configured to (i) cause the diaphragm to be moved to a starting position, (ii) actuate the actuating portion to cause the fluid contacting portion to pump over a full range of positive and negative pressures as read by the pressure transducer and to determine if the diaphragm flexes over the full range, (iii) if the diaphragm flexes over the full range, use the starting position of the diaphragm for an upcoming operation, and (iv) if the diaphragm does not flex over the full range, repeat (i) to (iv) moving the diaphragm to a different starting position.

In a twenty-sixth aspect of the present disclosure, which may be combined with any other aspect or portion thereof, the diaphragm is part of a tube in fluid communication with the fluid contacting portion of the fluid pump.

In a twenty-seventh aspect of the present disclosure, which may be combined with any other aspect or portion thereof, the fluid pump is a bellows, peristaltic, membrane or syringe pump.

In a twenty-eighth aspect of the present disclosure, which may be combined with any other aspect or portion thereof, a fluid system includes: a fluid pump including a fluid contacting portion and an actuating portion for actuating the fluid contacting portion; a pressure sensor; a cylinder and a piston moveably sealed within the cylinder, wherein the pressure sensor is in fluid communication with the cylinder; and a control unit configured to (i) actuate the actuating portion of the fluid pump to move a first distance to cause the fluid contacting portion of the fluid pump to deliver fluid, raising a pressure sensed by the pressure sensor from an initial pressure to a higher pressure, (ii) cause the piston to be retracted over a volume within the cylinder so that the pressure sensed by the pressure sensor returns to the initial pressure, (iii) assign the volume to be an actual volume of fluid delivered by the fluid contacting portion over the first distance moved by the actuating portion of the pump.

In a twenty-ninth aspect of the present disclosure, which may be combined with any other aspect or portion thereof, the control unit is further configured to cause (i) to (iii) to be repeated for at least one second distance moved by the actuating portion of the pump.

In a thirtieth aspect of the present disclosure, which may be combined with any other aspect or portion thereof, the pressure sensor includes a diaphragm separating a first side of the pressure sensor from a second side of the pressure sensor, the second side in operable communication with a pressure transducer, wherein the first side of the pressure sensor is in further communication with the cylinder, and wherein the pressures in (i) and (ii) are sensed by the pressure transducer.

In a thirty-first aspect of the present disclosure, which may be combined with any other aspect or portion thereof, the fluid pump is a bellows, peristaltic, membrane or syringe pump.

In a thirty-second aspect of the present disclosure, which may be combined with any other aspect or portion thereof, the first distance moved by the actuating portion corresponds to a first distance moved by the fluid contacting portion of the fluid pump.

In a thirty-third aspect, any of the features, functionality and alternatives described in connection with any one or more of FIGS. 1 to 17 may be combined with any of the features, functionality and alternatives described in connection with any other of FIGS. 1 to 17.

It is accordingly an advantage of the present disclosure to provide a relatively volumetrically accurate automated peritoneal dialysis ("APD") cycler.

It is another advantage of the present disclosure to provide an APD cycler that achieves relatively precise pressure control.

It is a further advantage of the present disclosure to provide a relatively quiet APD cycler.

It is yet a further advantage of the present disclosure to provide a relatively simple and low cost APD cycler.

It is yet another advantage of the present disclosure to provide a relatively simple disposable set.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1:
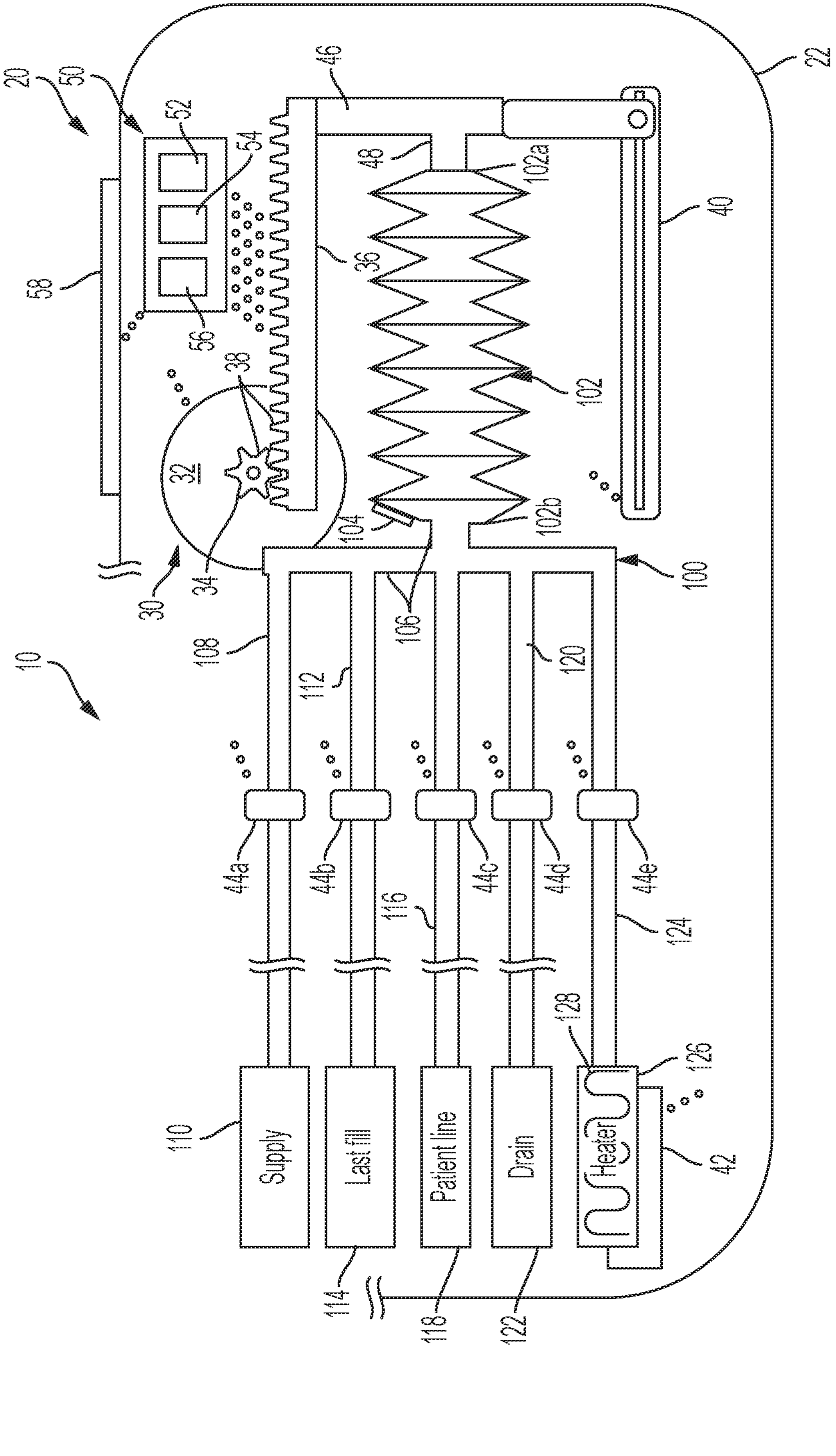
FIG. 1 is a top plan view of one embodiment for a bellows automated peritoneal dialysis ("APD") system of the present disclosure.

Referring now to the drawings and in particular to FIGS. 1, an automated peritoneal dialysis ("APD") system 10 includes and APD machine or cycler 20 that operates with a disposable set 100 having a bellows 102. APD machine or cycler 20 includes a housing 22 that houses or includes a linear actuator 30. One possible linear actuator 30 for driving bellows 102 includes a motor 32 that rotates its shaft to which a gear 34 is connected. Gear 34 forms the pinion that operates with a rack 36 of a rack and pinion having mating gear teeth 38. Motor 32 may be a stepper motor, brushed DC motor or brushless DC motor, for example. Certain types of motors 32, e.g., brushed DC motors, may be provided with a gearbox to lower its output speed.

In the illustrated embodiment, the rotational motion of the motor shaft is converted into translational motion by the rack 36 and pinion 34. Rack 36 is in direct or indirect mechanical communication with a moving end 102*a* of bellows 102, in the illustrated embodiment via a driver arm 46. End 102*b* of bellows 102 is fixed in FIG. 1. The translational motion of rack 36 and pinion 34 therefore causes expansion and compression of bellows 102 depending on the direction of rotation of the motor shaft of motor 32. In the illustrated embodiment, bellows 102 is fully expanded. To compress bellows 102, motor 32 causes pinion 34 to spin clockwise, which in turn causes rack 36 to move to the left and bellows 102 to compress accordingly. To expand bellows 102, motor 32 causes pinion 34 to spin counterclockwise, which in turn causes rack 36 to move to the right and bellows 102 to expand accordingly.

Other forms of linear actuation for system 10 may be used, such as (i) a motor coupled to a lead screw, ball screw, or high helix lead screw, (ii) a linear motor or (iii) a pneumatic cylinder. Each linear actuator 30 directly or indirectly contacts bellows 102 for its expansion and compression.

In the illustrated embodiment, linear actuator 30 operates with a slide potentiometer 40, which monitors the positon and movement of bellows 102. Alternative positional feedback devices are contemplated, e.g., motor 32 may be fitted with a motor encoder (not illustrated), which detects the rotational position of the motor shaft, which can be converted into a distance moved by rack 36 and pinion 34, and thus the distance moved by bellows 102, by knowing how much rack 36 moves per rotation, or partial rotation, of the shaft of motor 32 and pinion 34.

Volumetric accuracy for the APD system is determined in one embodiment by knowing the internal volume of bellows 102 and by detecting how much the bellows has been moved via one of the positional feedback devices described above. Volumetric accuracy also assumes the bellows to be completely full of fluid and thus fully primed. If needed, bellows 102 may be fitted with one or more hydrophobic membrane 104 to help "squeeze" the air out of the bellows during operation. Priming techniques for bellows APD system 10 are described below.

As discussed, disposable set 100 includes at least one bellows 102, which is expanded to perform a draw or fill stroke and is compressed to perform an expel or pump-out stroke. As illustrated in FIG. 1, bellows 102 connects to or is in fluid communication with a common input/output line 106 that feeds fluid into bellows 102 and accepts fluid from 102 bellows. Common input/output line 106 feeds or splits into multiple, e.g., five, separate lines, each interfacing with a valve, such as an electrically actuated solenoid valve or a pneumatically actuated valve. In the illustrated embodiment, the separate lines include a fresh dialysis fluid line 108 that extends to a fresh dialysis fluid supply or bag 110, a last fill fluid line 112 that extends to a last dialysis fluid supply or bag 114, a patient line 116 that carries fresh, heated dialysis fluid to a patient and used dialysis fluid from the patient via a patient connector 118 connected to the patient's transfer set (not illustrated), a drain line 120 that extends to a drain container 122, e.g., bag, or to a house drain such as a toilet or bathtub, and a heater line 124 that carries fresh dialysis fluid to a heater disposable 126, such as a container or bag having serpentine heating pathway 128.

In the illustrated embodiment, heater disposable 126 is heated by a heater 42 provided by APD machine or cycler 20. Heater 42 may be a batch or inline heater. For example, heater 42 may be a resistive plate heater, wherein heater disposable 126 is correspondingly either a batch or inline disposable. APD machine or cycler 20 further provides a valve 44*a* operable to selectively open and close fresh dialysis fluid line 108, a valve 44*b* operable to selectively open and close last fill fluid line 112, a valve 44*c* operable to selectively open and close patient line 116, a valve 44*d* operable to selectively open and close drain line 120, and a valve 44*e* operable to selectively open and close heater line 124. Valves 44*a* to 44*e* may be electrically actuated solenoid valves that are energized open and spring closed to be fail safe. Valves 44*a* to 44*e* may alternatively be pneumatically actuated.

Bellows 102 in the illustrated embodiment has in an embodiment has an accordion or concertina shape and may be made of a disposable plastic, such as polyvinyl chloride ("PVC"), polyethylene ("PE"), polyurethane ("PU") or polycarbonate. In an embodiment, the remainder of disposable set 100, including each of the lines and containers listed above, may be made of PVC or a medically approved non-PVC material.

In the illustrated embodiment of FIG. 1, APD machine or cycler 20 of system 10 includes a control unit 50. Control unit 50 is alternatively provided as a wireless user interface, such as a tablet or smartphone. In any case, as illustrated in FIG. 1, control unit 50 may include one or more processor 52, one or more memory 54, and a video controller 56 interfacing with a user interface 58, which may include a display screen operating with a touchscreen and/or one or more electromechanical button, such as a membrane switch. User interface 58 may also include one or more speaker for outputting alarms, alerts and/or voice guidance commands. Control unit 50 may also include a transceiver and a wired or wireless connection to a network, e.g., the internet, for sending treatment data to and receiving prescription instructions from a doctor's or clinician's server interfacing with a doctor's or clinician's computer.

Each of motor 32, potentiometer 40 (or encoder), heater 42 and valves 44*a* to 44*e* are under control of and/or output to control unit 50. Control unit 50 executes a treatment program or prescription prescribed by a doctor or clinician to perform the bellows and valve sequences described herein.

Figure 2:
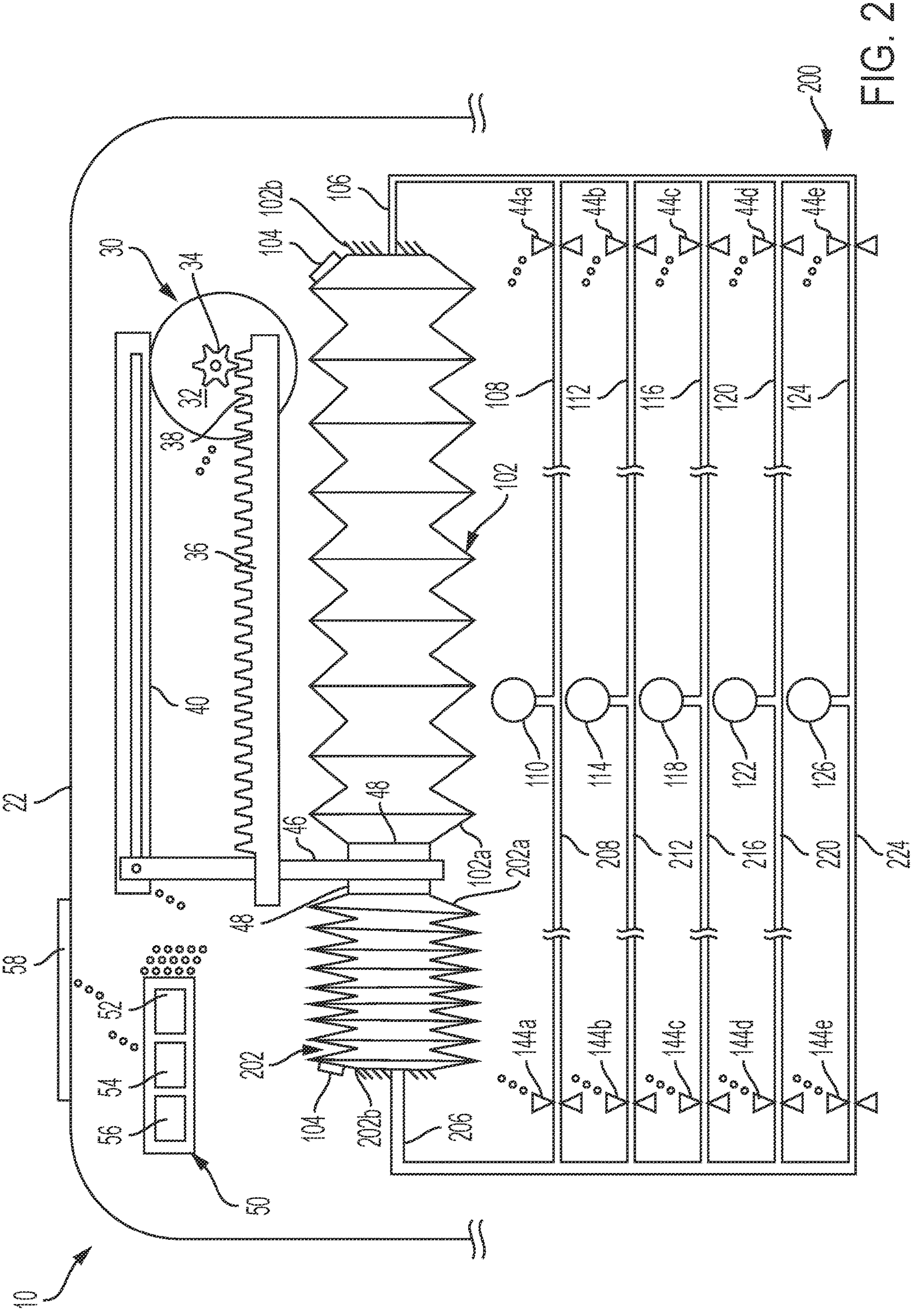
FIG. 2 is a top plan view of a second embodiment for a bellows automated peritoneal dialysis ("APD") system of the present disclosure.

Referring now to FIG. 2, in an alternative embodiment for system 10, it is contemplated to provide a set of two bellows 102 and 202 that are operated in an alternating manner to provide a more continuous flow and to increase flowrate. In an embodiment, driver arm 46 of linear actuator 30, e.g., motor 32 operably coupled to a rack 36 and pinion 34 meshing via gear teeth 38, is connected to both bellows 102 and 202 at a location so as to connect the two bellows together. In the illustrated embodiment, driver arm 46 is connected between moving ends 102*a* and 202*a* of bellows 102 and 202. In this manner, linear actuator 30 in (i) a first stroke moves in a first direction to expand a first bellows 102 or 202 to draw-in fluid and to compress the second bellows 202 or 102 to pump-out fluid and (ii) a second stroke moves in a second, opposing direction to expand the second bellows 202 or 102 to draw-in fluid and compress first bellows 102 or 202 to pump-out fluid. The result is a more continuous flow and an increased flowrate using basically the same linear actuator 30 as for the single bellows embodiment of system 10 of FIG. 1. Bellows 102 and 202 may each have a hydrophobic membrane 104 for priming as described herein and illustrated in FIG. 2.

Potentiometer 40 is provided again in FIG. 2. It stands to reason that bellows 102 and 202 move the same distance because both bellows are driven by the same rack 46. A single potentiometer 40 accordingly outputs both pump-in and pump-out distances to control unit 50. In an alternative embodiment, motor 32 is fitted with an encoder (not illustrated), such as an incremental or absolute encoder, which outputs to control unit 50 for use in determining volume of fluid pumped in and out, knowing the geometry of each bellows 102 and 202.

FIG. 2 illustrates that alternative disposable set 200 is in essence doubled versus disposable set 100. Besides the lines interfacing with bellows 102, including fresh dialysis fluid line 108 extending to fresh dialysis fluid supply or bag 110, last fill fluid line 112 extending to last dialysis fluid supply or bag 114, patient line 116 extending to patient connector 118, drain line 120 extending to drain container 122, and heater line 124 extending to heater disposable 126, disposable set 200 also provides lines for bellows, including dialysis fluid line 208 extending also to fresh dialysis fluid supply or bag 110, last fill fluid line 212 extending also to last dialysis fluid supply or bag 114, patient line 216 extending also to patient connector 118, drain line 220 extending also to drain container 122, and heater line 224 extending also to heater disposable 126. Additional lines 208, 212, 216, 220 and 224 operate with valves 144*a* to 144*e*, respectively, under control of control unit 50.

Disposable set 200 allows complete and independent control between bellows 102 and 202. Bellows 102 can pull fluid in from any source, while bellows 202 can pump out to any destination, and vice versa. It even possible to pull fluid from and push fluid to the same source/destination, e.g., for priming. The trade-off of system 10 of FIG. 2 is (i) the additional disposable cost of second bellows 202 and second set of lines 208, 212, 216, 220 and 224 to each of the sources and destinations and (ii) the additional cost and complexity of a second set of valves 144*a* to 144*e* and their respective control of the second set of lines 208, 212, 216, 220 and 224.

Single or dual bellows APD system 10 of the present disclosure contemplates different solutions for ensuring that motorized bellows 102, 202 does not create too much positive or negative fluid pumping pressure when delivering fresh dialysis to or removing used dialysis fluid from the patient via patient line 116, 216 and patient connector 118. Generally, it is desirable to limit patient pumping pressure for peritoneal dialysis to −1.5 psig for effluent removal and from +1.5 psig to +3.0 psig for fresh dialysis fluid delivery.

A first pressure control solution is to select motor 32 such that it is incapable of supplying (or is controlled not to supply) a positive or negative overpressure. The pressure that fluid is delivered to and removed from the patient is a function of the force exerted by linear actuator 30 and the area geometry of bellows 102, 202 and tubing 108, 112, 116, 120, 124, 208, 212, 216, 220 and 224. The maximum positive and negative patient pumping pressures are known (listed above) as is the geometry of the bellows and tubing. From these values, the maximum allowable force due to linear actuator 32 is able to be calculated. Knowing that force allows a maximum torque for motor 32 to be calculated so that a motor incapable of supplying a higher torque may be selected.

Motor Selection Control

Figure 3:
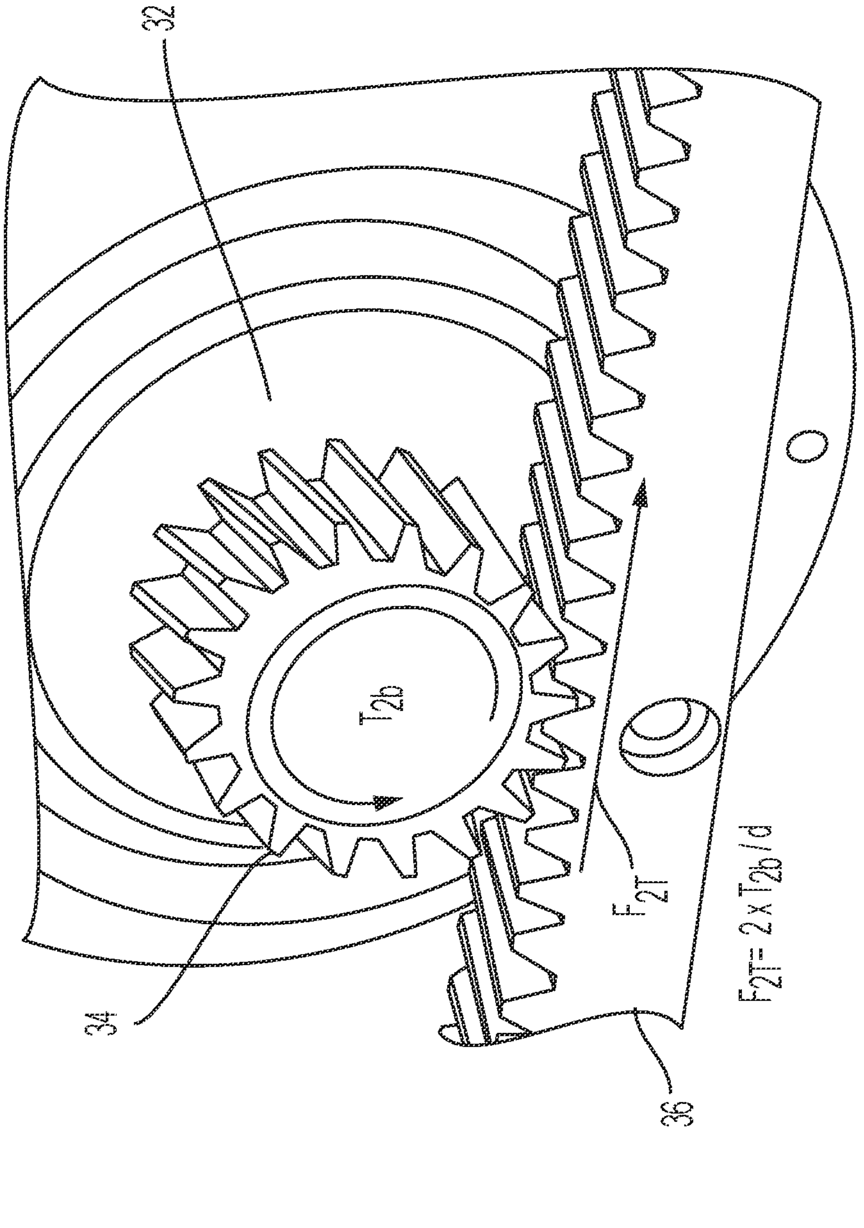
FIG. 3 is a perspective-sectioned view of a closer view of the rack and pinion linear actuator of the present disclosure illustrating an equation that may be used to determine a maximum allowable motor torque from a determined maximum allowable force provided by the linear actuator

FIG. 3 illustrates a relationship between output force of linear actuator 30, e.g., including rack 36 and pinion 34, and the torque outputted by motor 32. A different relationship is used for different linear actuators, e.g., the lead screw, ball screw, etc., arrangements listed above. In the illustrated equation, $F_{2T}$ is the force outputted by the rack 36 and pinion 34. $F_{2T}$ is set to be the maximum allowable force determined from the known maximum allowable pressure and the known geometry of bellows 102, 202 and tubing 108, 112, 116, 120, 124, 208, 212, 216, 220 and 224. Diameter d is the nominal diameter of pinion 34, which is also known. Thus the maximum allowable torque $T_{2b}$ outputted by motor 32 may be calculated. A single speed motor 32 having a maximum torque at or below the maximum is then selected. Or, a variable speed motor is selected for motor 32 and a low speed limit is set for patient pumping (motor torque has an inverse relationship with motor speed). Control unit 50 of APD system 10 of the present disclosure either causes a single speed motor 32 to be powered or maintains the low speed limit for variable speed motor 32 for patient pumping. Higher motor torques may be used for pumping from sources other than the patient, e.g., from supply container 110, last dialysis fluid supply or bag 114, or heater disposable 126. Higher motor torques may be used for pumping to sources other than the patient, e.g., to drain container 122 or heater disposable 126.

Force Sensor Control

A second pressure control solution contemplated for bellows APD system 10 of the present disclosure is to place a force sensor 48 (load cell or strain gauge) in contact with bellows 102, 202, e.g., between driver arm 46 and bellows 102, 202 as illustrated in FIGS. 1 and 2. In this manner, force sensors 48 are located so as to sense the force applied by driver arm 46 of linear actuator 30 on the bellows. But instead of calculating a maximum allowable motor torque for patient pumping, the actual force due to the linear actuator 30 is measured. The measurement may be used as feedback to control unit 50, which causes the speed of motor 32 to be varied to ensure that the resulting force due to linear actuator 30 is below the maximum allowable force. The maximum allowable force due to the linear actuator is calculated again knowing the maximum allowable positive and negative patient pumping pressures and the geometry of the bellows 102, common input/output line 106, 206 and/or patient line 116, 216. To reduce noise leading to error, such as force to torque conversion, current to torque conversion and current sensing error, it is contemplated to locate the force sensors 48 close the item to be sensed, namely, bellows 102. Doing so reduces or eliminates these errors.

Direct Pressure Control

Figure 4:
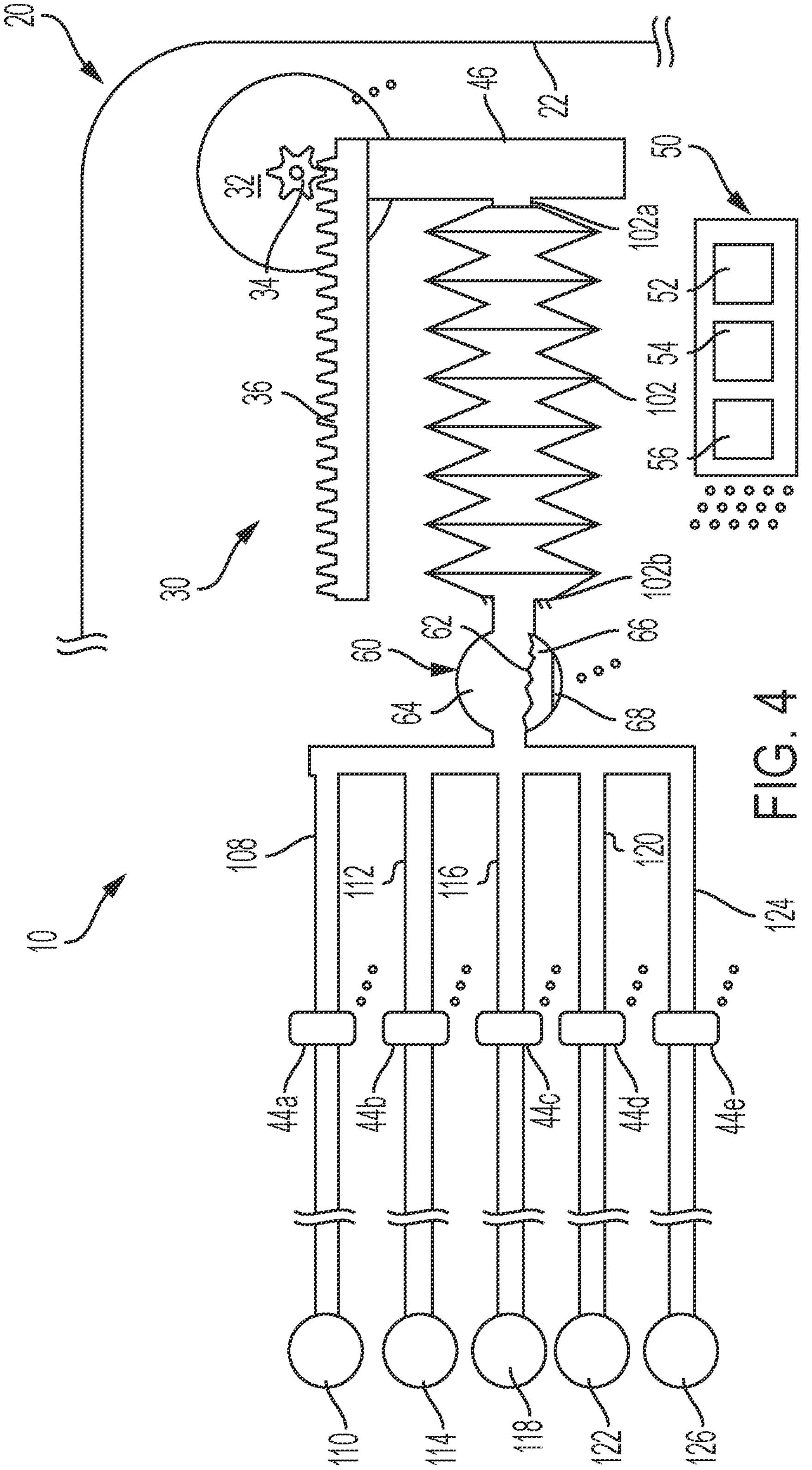
FIG. 4 is a top plan view of one embodiment for a bellows automated peritoneal dialysis ("APD") system of the present disclosure having an integrated pressure sensor for pressure control.
Figure 5:
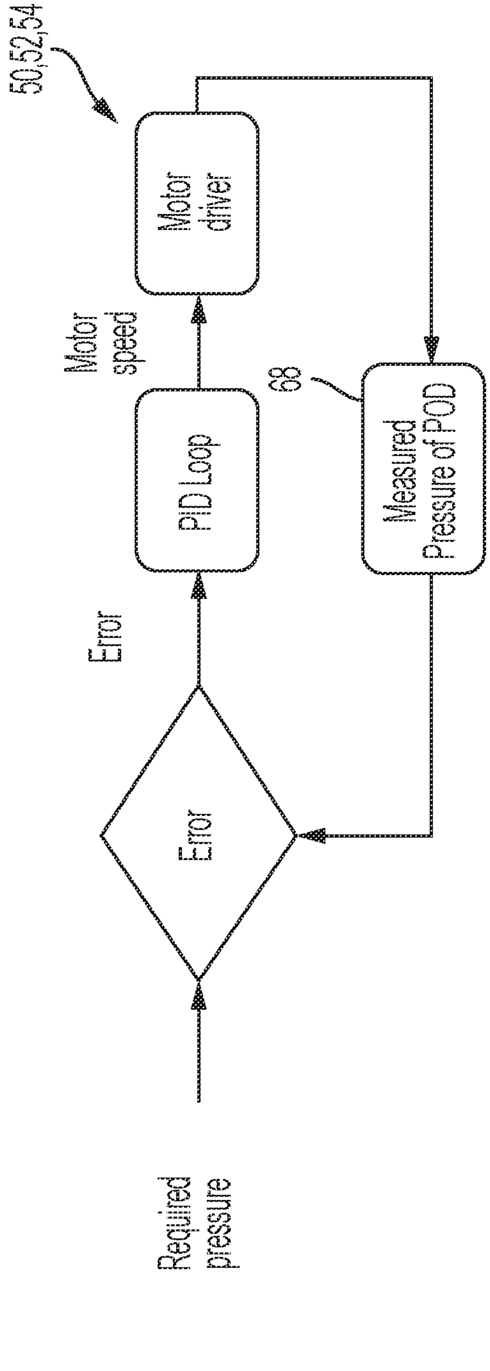
FIG. 5 is a schematic diagram illustrating one embodiment of a pressure feedback loop used with the pressure sensor of FIG. 4.

FIGS. 4 and 5 illustrate a third pressure control solution contemplated for bellows APD system 10 of the present disclosure, which is to add a pressure sensing module or pod 60 that measures fluid pressure directly and obviates the need to know the geometry of bellows 102, 202 and tubing 108, 112, 116, 120, 124, 208, 212, 216, 220 and 224, and the need to determine maximum allowable forces. Pressure pod 60 in the illustrated embodiment incudes a membrane 62 that separates a fluid pumping side 64 of the pod from an air transducer sensing side 66 of the pod. The flexibility of membrane 62 allows pressure on either side of the membrane to equilibrate, such that the pressure of any of the different fluids discussed herein equals the sensed transmission fluid or air pressure. FIG. 4 illustrates that a pressure transducer 68 may be provided on transducer sensing side 66 of pressure pod 60. Alternatively, transducer 68 may be located at the end of a transmission fluid or air tube (not illustrated).

Transducer 68 outputting to control unit 50 measures the pressure of transmission fluid or air, which equals that of the PD fluid, patient fluid, heated fluid, effluent or other fluid. FIG. 5 illustrates that processing 52 and memory 54 of control unit 50 uses the pressure signal as feedback to vary the speed of the electronic driver (may be a separate card of control unit 50) for bellows motor 32 to make sure that the resulting positive or negative fluid pressure does not exceed an allowable limit. The pressure limits may be different for different fluid sources and destinations. In FIG. 5, control unit 50 sets a pressure to be achieved (not just avoiding a pressure limit), which is compared against a pressure signal measured by transducer 68, which may be provided at cycler 20. The difference may be fed into a control algorithm, e.g., a proportional, integral, differential ("PID") algorithm, which attempts to reduce the difference between the commanded pressure and the measured pressure to zero, and results in an output to the electronic motor driver. The above analysis is performed on some periodic frequency. It should be appreciated that in system 10 of FIG. 2, each bellows 102 and 202 may cooperate with a pressure sensor or pod 60 outputting to control unit 50 as described herein.

Figure 6:
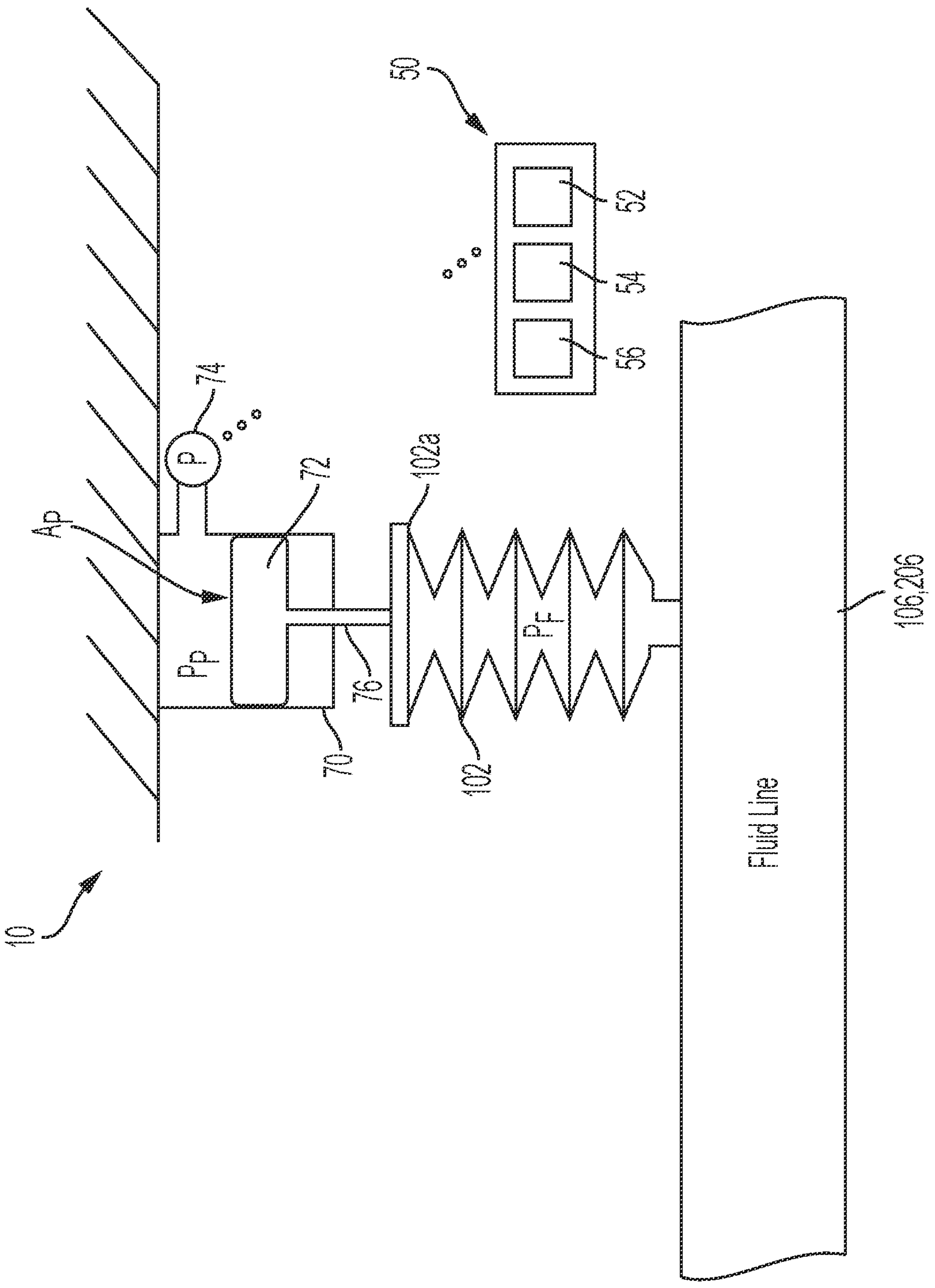
FIG. 6 is a top plan view of one embodiment for a bellows automated peritoneal dialysis ("APD") system of the present disclosure having an alternative integrated pressure sensor for pressure control.

FIG. 6 illustrates an alternative pressure sensing embodiment for system 10, in which a pressure measurement cylinder 70 is provided and fixed to a wall of housing 22. A piston 72 is fitted in a sealed manner, e.g., via an o-ring seal, within pressure measurement cylinder 70. A pressure transducer 74 is located so as to be in fluid communication with cylinder 70 above piston 72. Pressure transducer 74 outputs to control unit 50 and is provided by cycler 20 in one embodiment. A piston rod 76 extends from a head of piston 72 to the outside of pressure measurement cylinder 70. Piston rod 76 is placed in mechanical communication with moving end 102*a* of bellows 102 (and 202*a* of bellows 202 if provided). Bellows 102 via piston 72 exerts a force on the air within pressure measurement cylinder 70. When equilibrium is reached, the force of compressed air is equal to the force exerted by bellows 102. The force is deduced from the reading of pressure transducer 74 via the equation $P_f = P_p \times A_p/A_b$, where $P_p$ is the pressure of the piston, $A_p$ is the cross-section area of pressure measurement cylinder 70 and $A_b$ is the nominal cross-section area of pressure measurement of bellows 102. Hence, the fluid pressure $P_f$ is calculated using the measurement of pressure transducer 74.

As mentioned above, it is important to prime the bellows APD system 10 for volumetric accuracy and to prevent the delivery of air to the patient. In one priming sequence under control of control unit 50 of the present APD system, the single bellows 102 or dual bellows 102, 202 pump is caused to first prime the supply line 108, 208. If the volume of a single stroke of the bellows pump is less than the volume of supply line 108, 208, then it is contemplated to open supply line valve 44*a*, 144*a* on the draw stroke of the bellows pump, and then to close that valve 44*a*, 144*a* and open drain valve 44*d*, 144*d* to push air via the subsequent pump-out stroke of the bellows 102, 202 to drain. The above sequence is repeated until the supply line is fully primed, which may be detected by a sensor (not illustrated) located at the common input/output line, or determined empirically to require a certain amount of pump strokes.

The priming operation of supply line 108, 208 is then repeated for all supply lines and last bag line 112, 212. With the supply and last bag lines primed, fresh dialysis fluid is then used to prime patient line 116, 216 up to patient connector 118, which may be set at a certain elevation/height. Patient connector 118 is alternatively placed next to a sensor that determines when the patient line is fully primed. Heater line 124, 224 is then primed at least up to its interaction with heater valve 44*e*, 144*e*. Drain line 120, 220 may or may not be primed, e.g., may be primed up to drain line valve 44*d*, 144*d*.

Alternatively or additionally to the above sequence, fixed ends 102*b*, 202*b* may be elevated during priming to help direct air into common input/output lines 106, 206, which aids in sending the air to drain container 122 or to a house drain. Further alternatively or additionally, hydrophobic membranes 104 may be fitted to bellows 106, 206 to aid the priming of same.

Tube Pressure Sensor, Diaphragm Adjustment, Inline Pressure Pod

Figure 7:
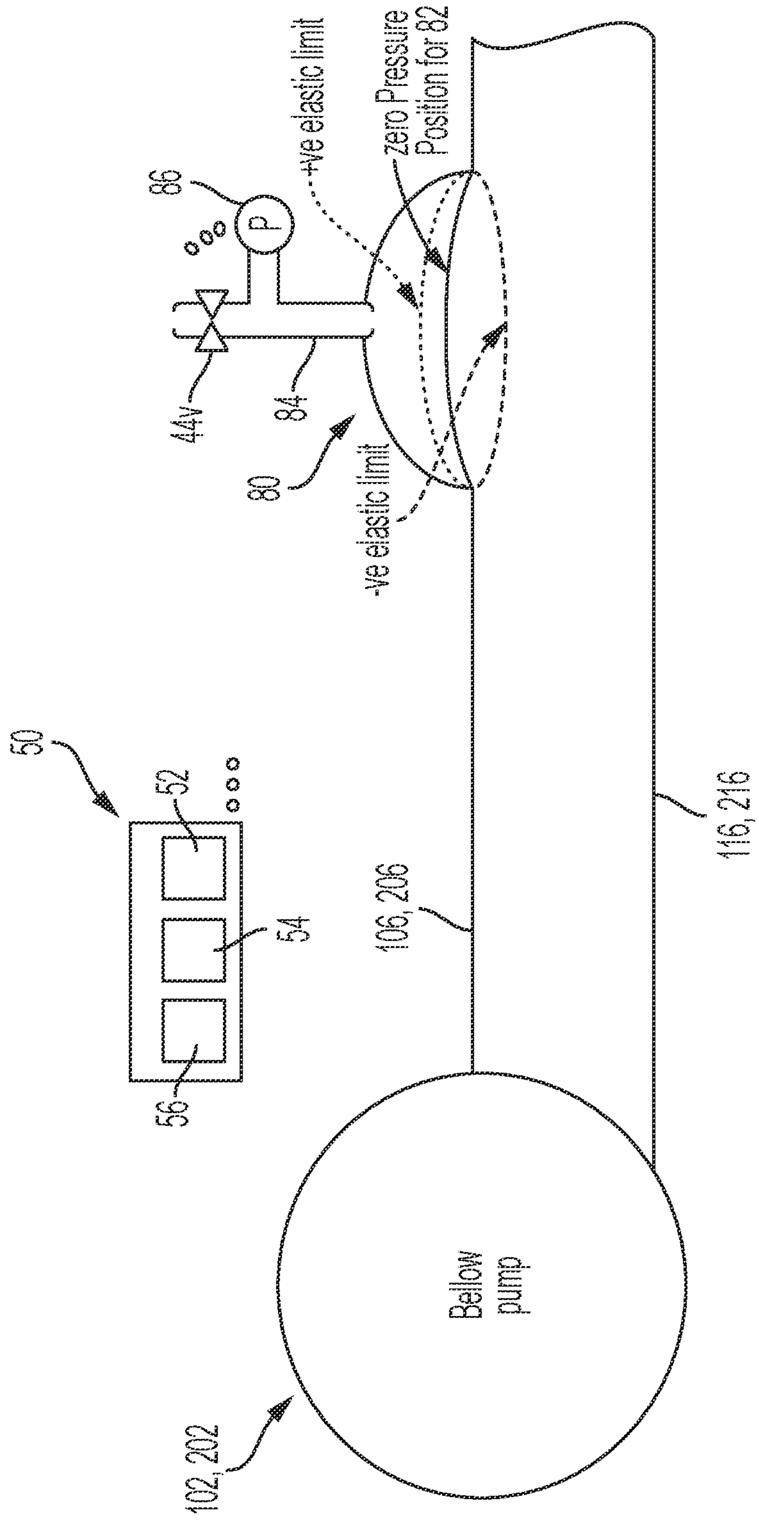
FIG. 7 is a schematic view illustrating an alternative pressure sensing embodiment in which a pressure measurement is taken directly along a fluid line.

FIG. 7 illustrates another alternative pressure sensing embodiment for system 10, in which a pressure measurement is taken directly along a fluid line, for example along common line 106, 206 or patient line 116, 216. In the illustrated embodiment, a dome 80 is welded to or formed above a pressure sensing area or diaphragm 82 of common line 106, 206 or patient line 116, 216. Common line 106, 206 or patient line 116, 216 may include an increased diameter section (not illustrated), if needed, onto which dome 80 and pressure sensing diaphragm 82 are located. Pressure sensing area or diaphragm 82 may have the same curvature and be of the same thickness as the rest of common line 106, 206 or patient line 116, 216. Alternatively, pressure sensing area 82 is either one or both of flattened and/or thinner that the rest of common line 106, 206 or patient line 116, 216. For example, pressure sensing diaphragm 82 could be a thin circular membrane that is welded into a hole formed in common line 106, 206 or patient line 116, 216, after which pressure dome 80 is welded to the fluid line above the pressure sensing diaphragm 82. The welding may be via any of ultrasonic welding, heat sealing or solvent bonding.

A pressure transmission line 84 extends to a pressure transducer 86, which communicates with control unit 50 and may be provided at cycler 20. The output of pressure transducer 86 may be used in the manner discussed in connection with FIG. 5. Pressure transmission line 84 also extends to a vent valve 44*v*, which is under control of control unit 50. Vent valve 44*v* is used in one embodiment to help ensure that pressure sensing diaphragm 82 is located in a proper "zero" pressure position in FIG. 7, such that it will flex over an entire range of pressures without reaching a positive +ve pressure elastic limit or a negative −ve pressure elastic limit.

Figure 8:
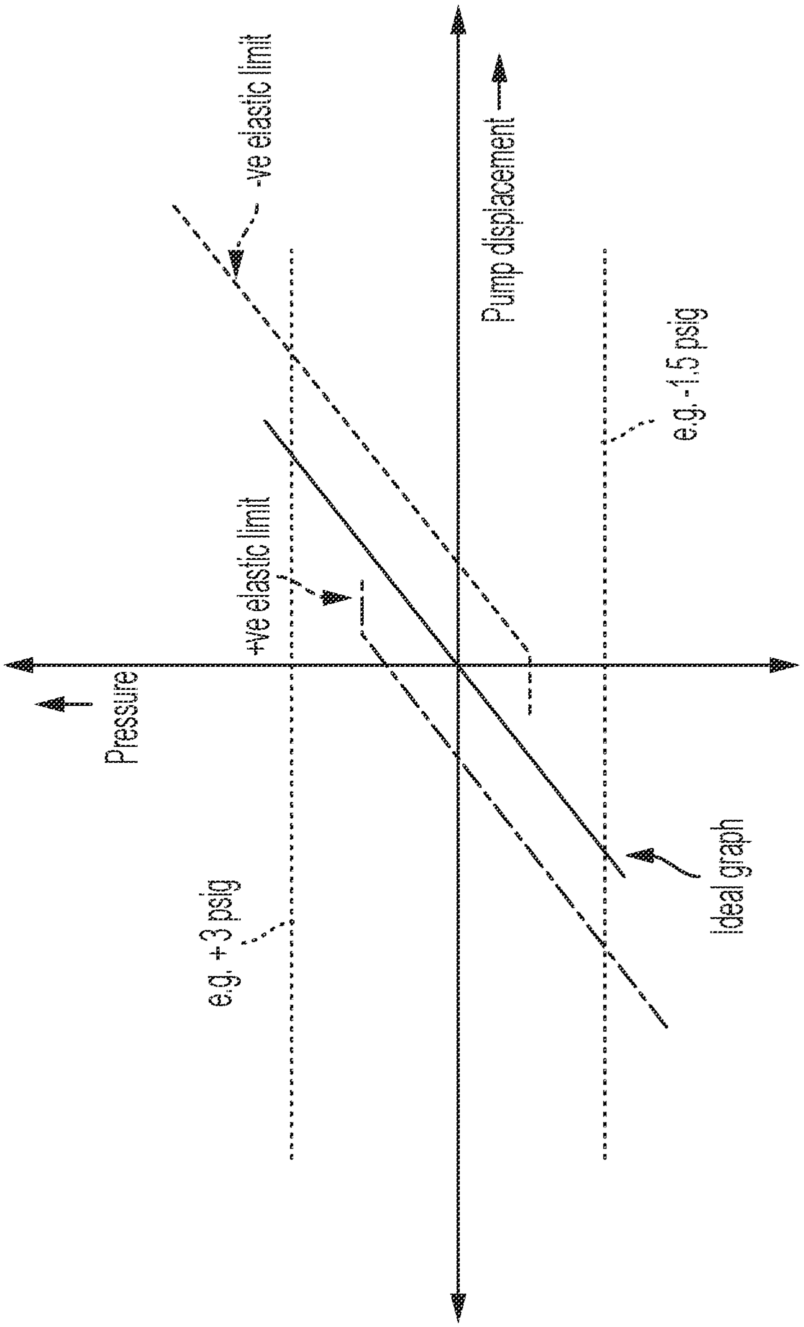
FIG. 8 is a schematic view illustrating one embodiment for setting a position of a pressure sensing diaphragm so that it senses properly over a full range of positive and negative pressures.

FIG. 8 illustrates via the plot line to the left (long/short dash) that if pressure sensing diaphragm 82 is initially too close to the positive pressure +ve limit at zero pressure, then the diaphragm will reach its positive elastic limit +ve (flat lining) prior to the upper, positive target pressure (e.g., +3 psig) level being reached. FIG. 8 also illustrates via the plot line to the right (constant dash) that if pressure sensing diaphragm 82 is initially too close to the negative pressure −ve limit at zero pressure, then the diaphragm will reach its negative elastic limit −ve (flat lining) prior to the lower, negative target pressure (e.g., −1.5 psig) level being reached.

FIG. 8 illustrates via the plot line in the middle (solid line) a situation in which pressure sensing diaphragm 82 is initially located in a suitable position at zero pressure, such that it flexes and outputs a pressure change over an entire range for both the positive and negative target pressure limits. Referring additionally to FIG. 7, it is contemplated that at a desirable time, e.g., prior to treatment and/or during a patient dwell, to close line valves 44*a* to 44*e* and vent valve 44*v* and place common line 106, 206 or patient line 116, 216 under a known positive or negative pressure to move pressure sensing diaphragm 82 outwardly or inwardly, respectively, a small distance. Next, control unit 50 opens vent valve 44*v* so that pressure sensor 86 reads zero pressure. Control unit 50 then closes vent valve 44*v* and attempts to reach both positive and negative target pressures. If control unit 50 sees that either the positive or negative target pressure cannot be met (diaphragm 82 meets an elastic limit), then control unit 50 repeats the above procedure correcting the zero pressure position of pressure sensing diaphragm 82 in the proper direction. For example, if the positive pressure target cannot be met, then control unit 50 causes pressure sensing diaphragm 82 (*i*) to move less outwardly, (ii) to not move at all, or (iii) to move inwardly in the next attempt to reach both positive and negative target pressures. If on the other hand the negative pressure target cannot be met, then control unit 50 causes pressure sensing diaphragm 82 (*i*) to move less inwardly, (ii) to not move at all, or (iii) to move outwardly in the next attempt to reach both positive and negative target pressures.

The test is repeated, each time adjusting the diaphragm position based on the previous result until a suitable starting position for diaphragm 82 is detected. Control unit 50 remembers the pressure associated with such position and applies such pressure on the next patient fill or patient drain before opening vent valve 44*v* to zero out the pressure in preparation for the fill or drain.

To summarize the above methodology for system 10, in a first step, line valves 44*a* to 44*e* and vent valve 44*v* are closed and common line 106, 206 or patient line 116, 216 are placed under a known positive or negative starting pressure to move pressure sensing diaphragm 82 outwardly or inwardly. In a second step, vent valve 44*v* is opened so that the pressure in dome 80 falls to zero. In a third step, the vent valve 44*v* is closed and control unit 50 operates bellows pump 102, 202 to attempt to perform a pressure sweep to reach both positive and negative target pressures. If both pressure limits can be reached or met, then in a fourth step, control unit 50 stores the pressure from first step so as to be associated with the successful position and causes such pressure to be applied on the next patient fill or patient drain before opening vent valve 44*v* to zero out the pressure in preparation for the fill or drain. If either pressure limit cannot be reached or met, then in a fifth step, control unit 50 modifies the pressure in a direction (more or less positive or more or less negative) that attempts to correct the limit that could not be reached or met and returns to the first step, but now using the modified pressure. The above steps are repeated until a suitable pressure and position for diaphragm 82 is determined.

System 10 is also configured to determine if diaphragm 82 has moved from its starting position, e.g., using a recalibration sequence. For example, during a patient dwell phase, system 10 applies the starting pressure that caused diaphragm 82 to move over the entire pressure range, so that the diaphragm moves to the designated position. Vent valve 44*v* is then opened to zero the pressure. System 10 then attempts to meet both pressure limits using the diaphragm and applying a pressure sweep. If both limits are met then the starting pressure is maintained. If not, then the procedure described above is repeated until a new starting pressure for diaphragm 82 is determined and used for the next fill or drain.

It should be appreciated that the dome 80 of FIG. 7 and its associated functionality in connection with FIG. 8 may be used for any type of fluid delivery system using any type of pump, such as a bellows, peristaltic, membrane or syringe pump to pump any desired fluid, such as peritoneal or hemodialysis dialysis fluid, blood, replacement fluid, heparin, citrate, an intravenous drug, saline, lactated ringers, and/or a nutritional fluid. It is contemplated to use such structure and functionality for any type of therapy, treatment or modality, including but not limited to, plasmapherisis, hemodialysis ("HD"), hemofiltration ("HF") hemodiafiltration ("HDF"), continuous renal replacement therapy ("CRRT"), peritoneal dialysis ("PD"), intravenous drug delivery, and nutritional fluid delivery.

Figure 9A:
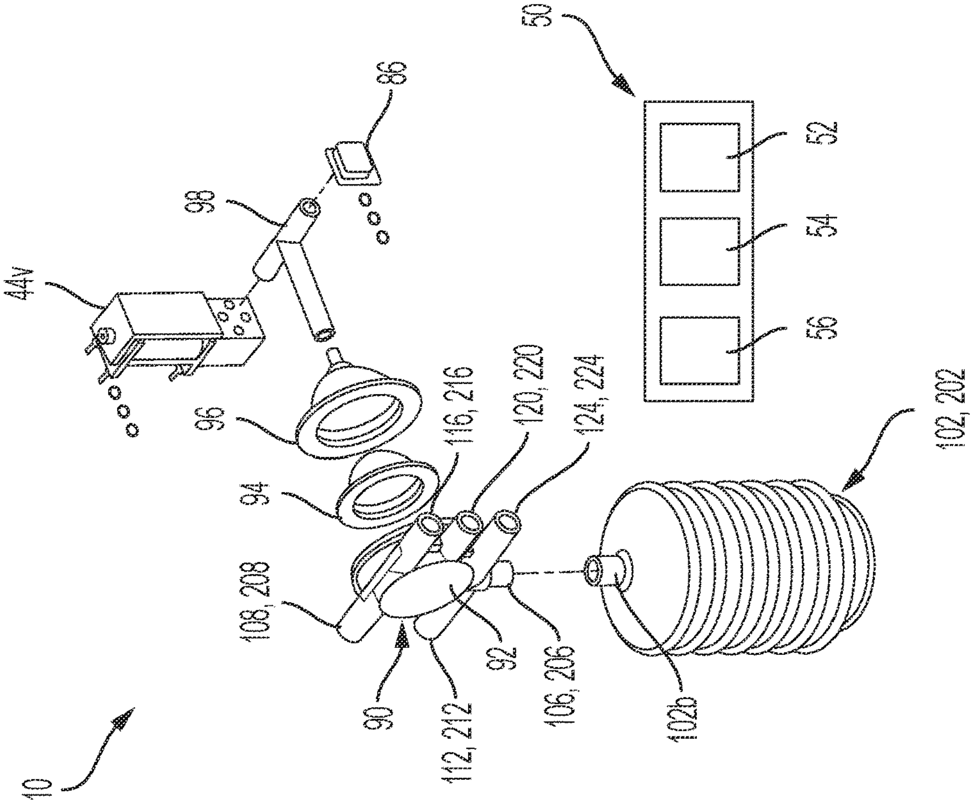
FIGS. 9A and 9B are exploded perspective views of one embodiment of a pod pressure bellows APD system of the present disclosure.
Figure 9B:
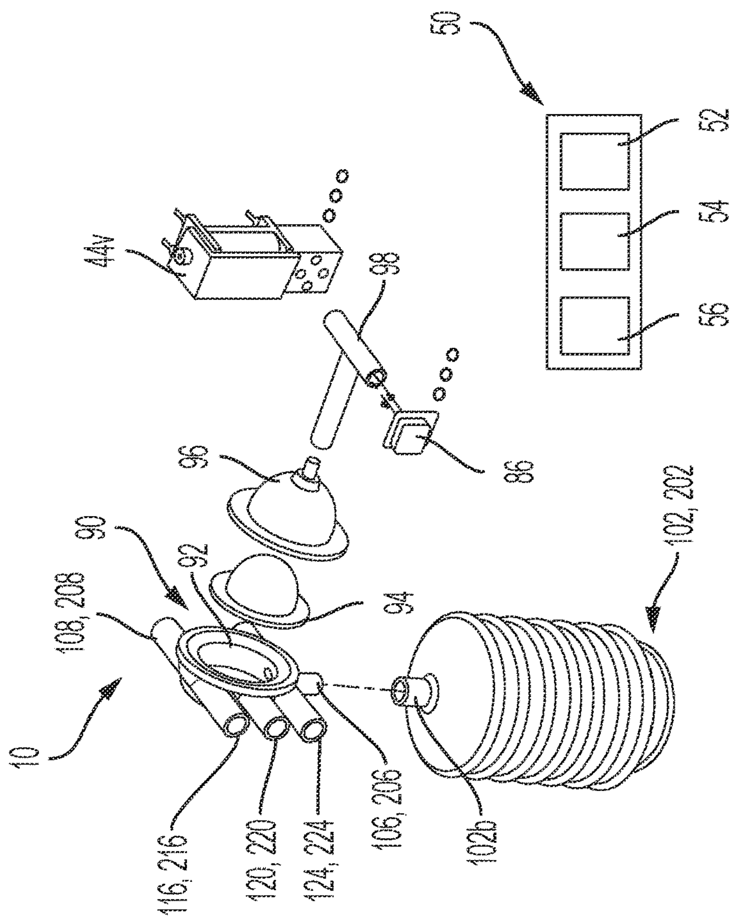

FIGS. 9A and 9B are perspective views of one configuration for bellows system 10 having an integrated pressure sensor of the present disclosure. Here system 10 includes a manifold 90, which may be a rigid plastic molded manifold made of any of the materials discussed herein. Manifold 90 forms a common line or port 106, 206 that seals to outlet end 102*b* of bellows 102, 202. Manifold also 90 forms ports for fresh dialysis fluid lines 108, 208, last fill fluid lines 112, 212, patient lines 116, 216, drain lines 120, 220 and heater lines 124, 224. Manifold 90 includes a common fluid chamber 92 that interfaces with a fluid side of flexible, pressure transmitting diaphragm 94. Manifold 90 and diaphragm 94 are disposable in one embodiment.

Common fluid chamber 92 seals to an air chamber 96, trapping pressure transmitting diaphragm 94 between chambers 92 and 96. Air chamber 96 in the illustrated embodiment connects in a sealed manner, e.g., via compression or luer connection, to air transmission line 98, which extends to a vent valve 44*v* under control of control unit 50 and to a pressure transducer 86 outputting to control unit 50. Air chamber 96, air transmission line 98, vent valve 44*v* and pressure transducer 86 are each reusable components provided as part of cycler 20 in one embodiment. The diaphragm 94 positioning routine described in connection with FIG. 8 may also be performed with the chamber 92 and diaphragm 94 configuration of system 10 illustrated in FIGS. 9A and 9B.

Calibration

Referring now to FIGS. 10 to 14, structure and methodology are added to system 10 to allow the system to self-calibrate how much fresh or used dialysis fluid is actually moved over a partial or full stroke of bellows 102, 202. The self-calibration allows for variance between different bellows 102, 202 of different systems. The self-calibration also allows the manufacturing tolerances for the bellows to be less stringent. For example, suppose bellows 102, 202 is sized to deliver 50 milliliters ("ml") per stroke. Without the calibration routine of FIGS. 10 to 14, bellows 102, 202 may have to be manufactured so as to have an actual stroke volume of 49 to 51 ml/stroke for example. Providing the calibration routine of FIGS. 10 to 14, on the other hand, may allow bellows 102, 202 of system 10 to have a considerably wider stroke volume, e.g., 40 to 60 ml/stroke.

FIGS. 10 to 14 use the same numbering provided in connection with FIGS. 9A and 9B. It should be appreciated however that the structure and methodology (e.g., implemented via control unit 50) associated with the calibration routine of FIGS. 10 to 14 may be used with any of the alternative embodiments for system 10 discussed herein. Additionally, air transmission line 98 is illustrated as extending to an air cylinder 70. A piston head 72 is provided in a sealed, e.g., via an o-ring seal, and moveable manner within air cylinder 70. A piston rod 76 extends from piston head 72 to a linear actuator 130 under control of control unit 50. Linear actuator 130 in one embodiment includes a rotating nut motor 132, wherein piston rod 76 includes a lead screw or ball screw that threads directly into rotating nut motor 132. Linear actuator 130 is alternatively of a rack and pinion arrangement or includes a stepper motor coupled to a lead screw or ball screw. Linear actuator 130 additionally includes a potentiometer or encoder as discussed herein that outputs to control unit 50 for determining precisely how far piston head 72 moves within cylinder 70.

Figure 10:
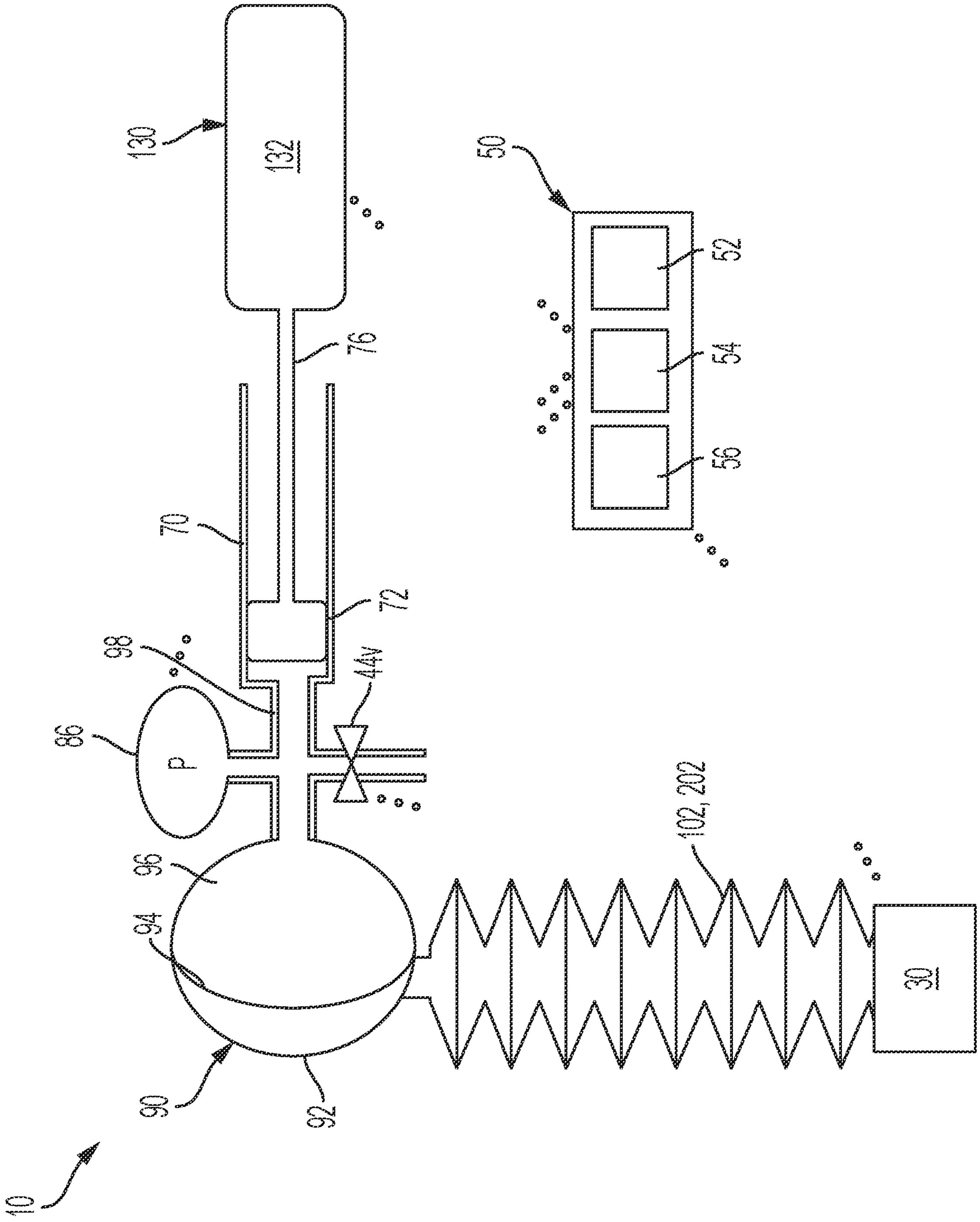
FIGS. 10 to 14 are schematic and graphical views of one embodiment for a self-calibrating bellows volume accuracy routine and associated structure of the present disclosure.
Figure 11:
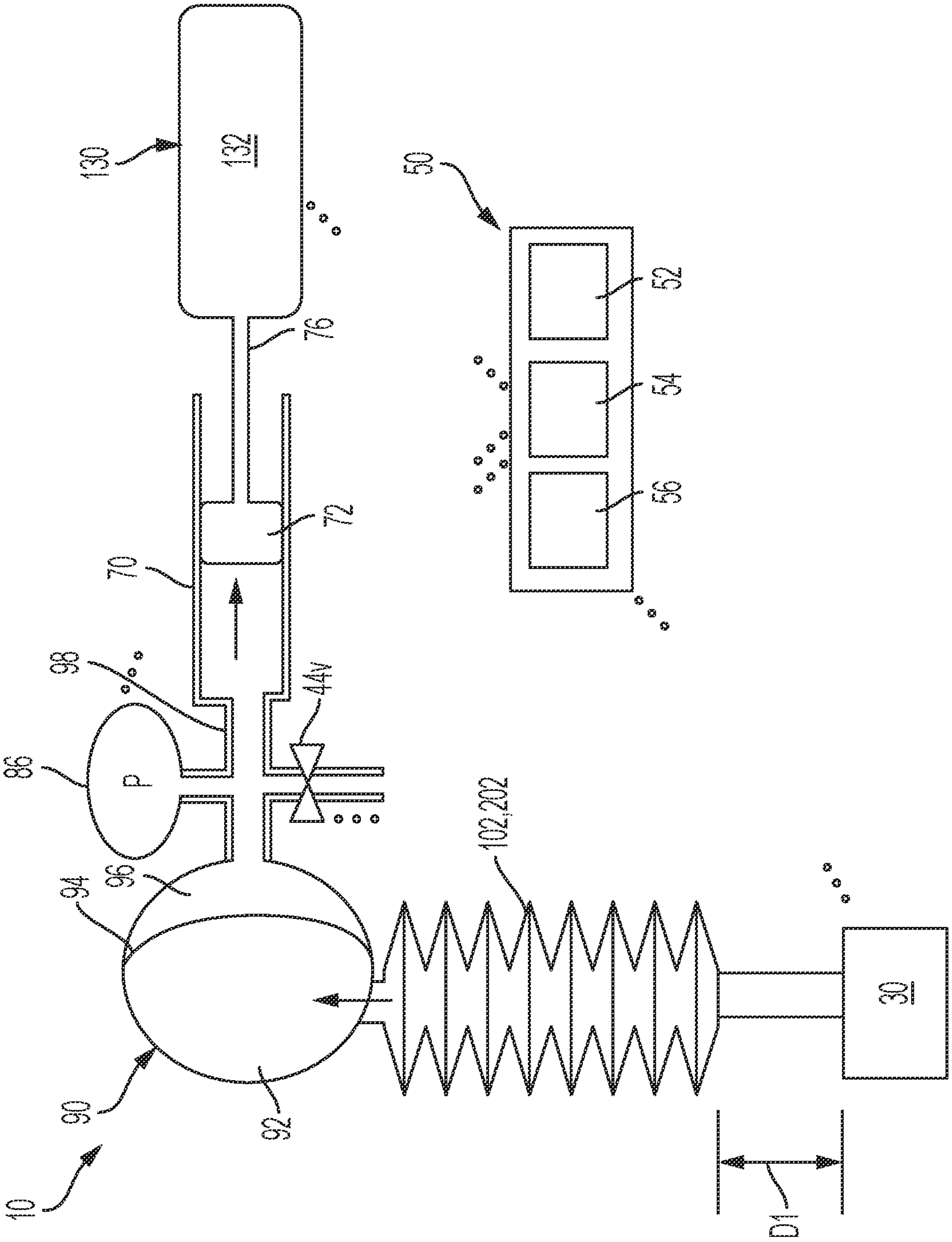

In FIG. 10, the first step of the calibration routine is to record a known initial pressure $P_{initial}$, which can be a zero pressure or a slightly positive pressure. FIG. 11 illustrates that in a second step, control unit 50 causes bellows 102, 202 to be advanced a first distance (to D1), pushing fluid into fluid chamber 92 and increasing the pressure as measured at pressure transducer 86 to a higher pressure $P_{higher}$. Linear actuator 130 then retracts piston rod 76 and piston head 72 until the measured pressure returns from $P_{higher}$ to $P_{initial}$. The potentiometer or encoder measures that distance that piston rod 76 and piston head 72 have been retracted, wherein control unit 50 knowing the cross-sectional area of cylinder 70 calculates the volume associated with the retracted distance. Because the starting and ending pressures are equal at $P_{initial}$, the volume of fluid displaced by bellows 102, 202 over the first distance (to D1) is equal to the known volume of air through which piston head 72 traveled. Control unit 50 records this first volume displaced and assigns it to the first distance (to D1) moved by the bellows.

Figure 12:
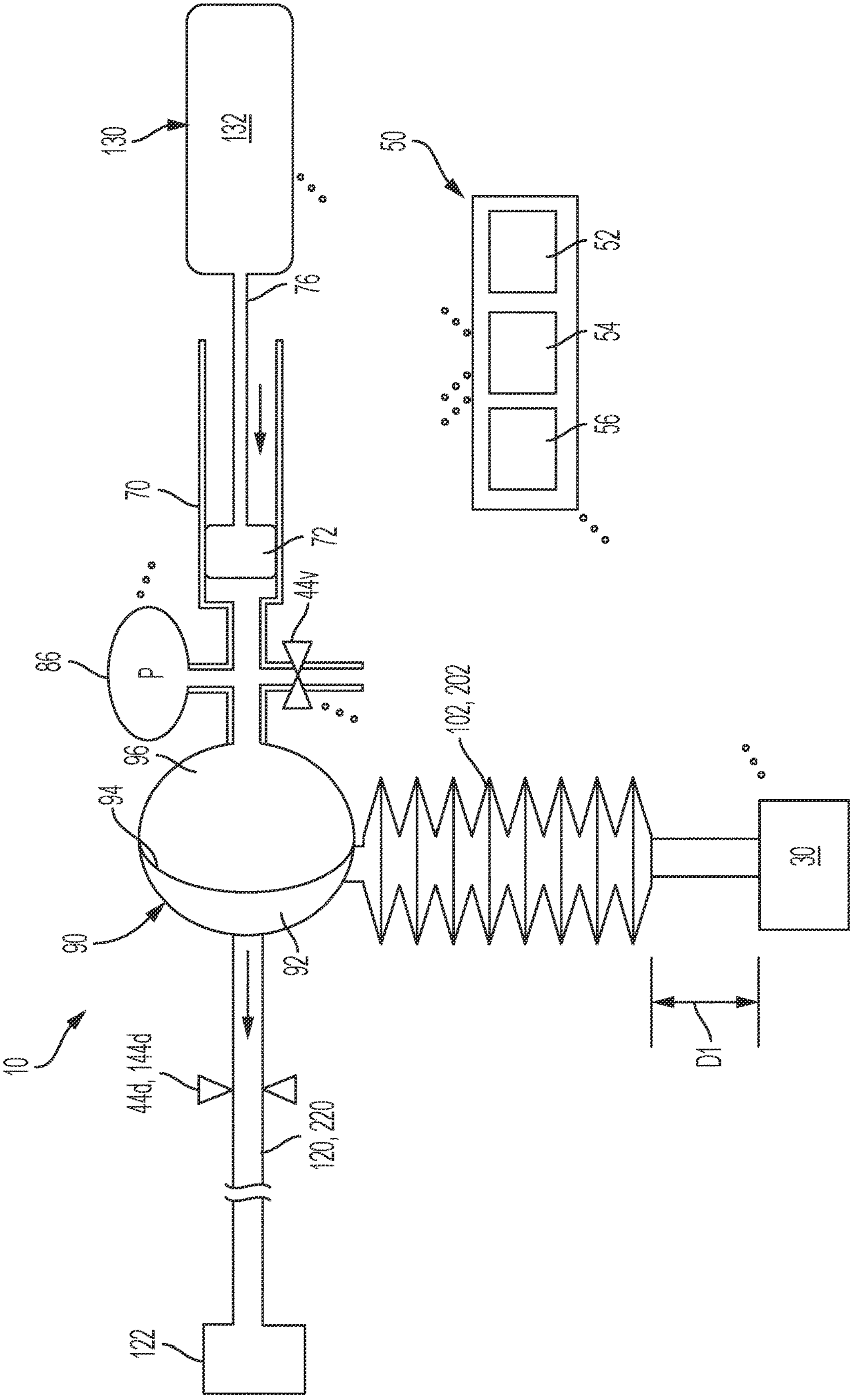
Figure 13:
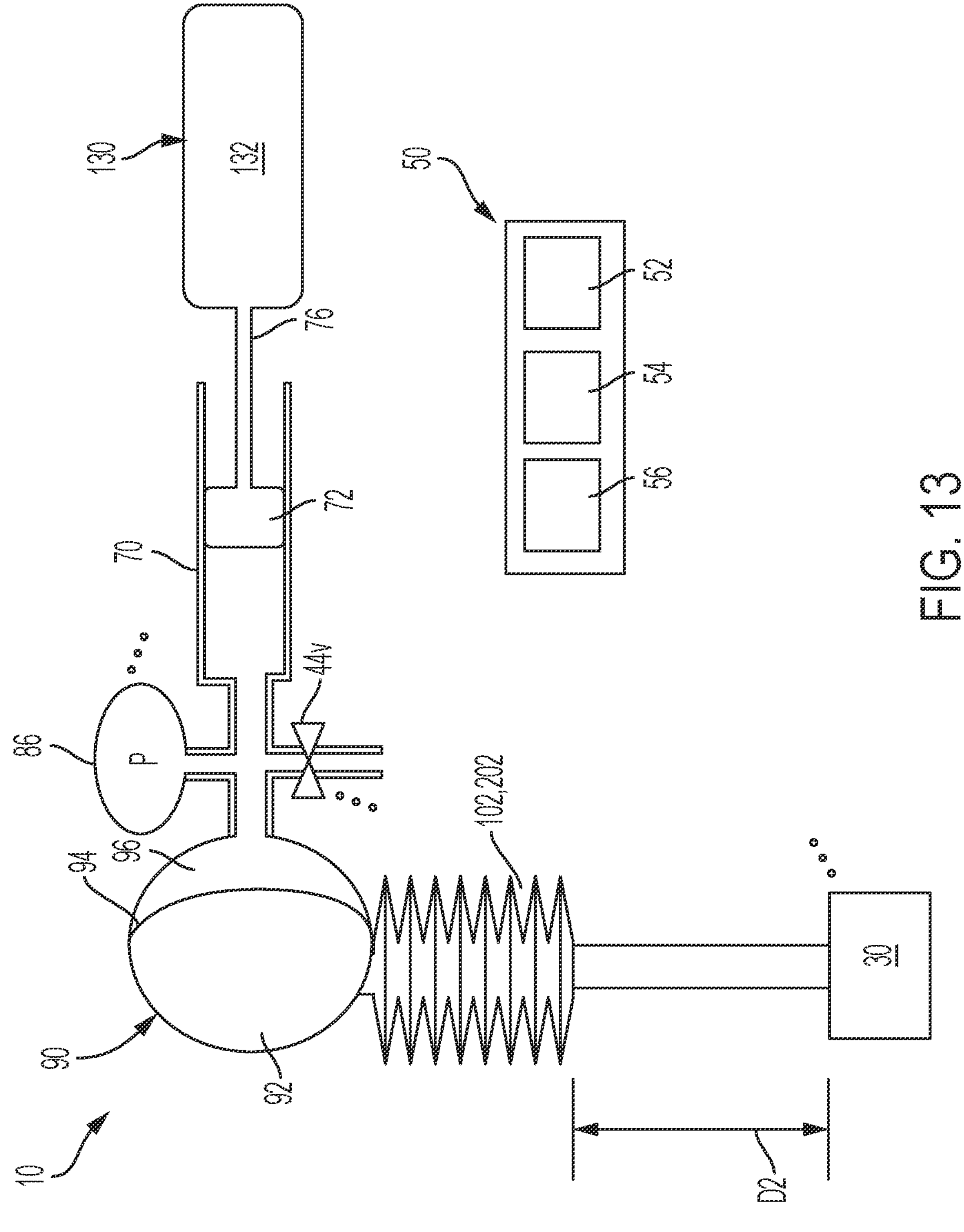

In FIG. 12, control unit 50 in a third step maintains bellows 102, 202 at the first distance position (D1) and opens drain valve 44*d*, 144*d* to allow linear actuator 130 to push at least some of the fluid within fluid chamber 92 to drain 122. In FIG. 13, the action taken by control unit 50 in connection with FIG. 11 is repeated in a fourth step, but here causing bellows 102, 202 to be advanced a second distance (which may be the same or different than the first distance) to D2, pushing fluid into fluid chamber 92 and increasing the pressure as measured at pressure transducer 86 from an initial pressure $P_{initial}$ to a higher pressure $P_{higher}$. Linear actuator 130 then retracts piston rod 76 and piston head 72 until the measured pressure returns from $P_{higher}$ to $P_{initial}$. The potentiometer or encoder measures the distance that piston rod 76 and piston head 72 have been retracted, wherein control unit 50 knowing the cross-sectional area of cylinder 70 calculates the volume associated with the retracted distance. Because the starting and ending pressures are equal at $P_{initial}$, the volume of fluid displaced by bellows 102, 202 over the second distance (to D2) is equal to the known volume of air through which piston head 72 traveled. Control unit 50 records this second volume displaced and assigns it to the second distance (to D2) moved by bellows 101, 102.

Figure 14:
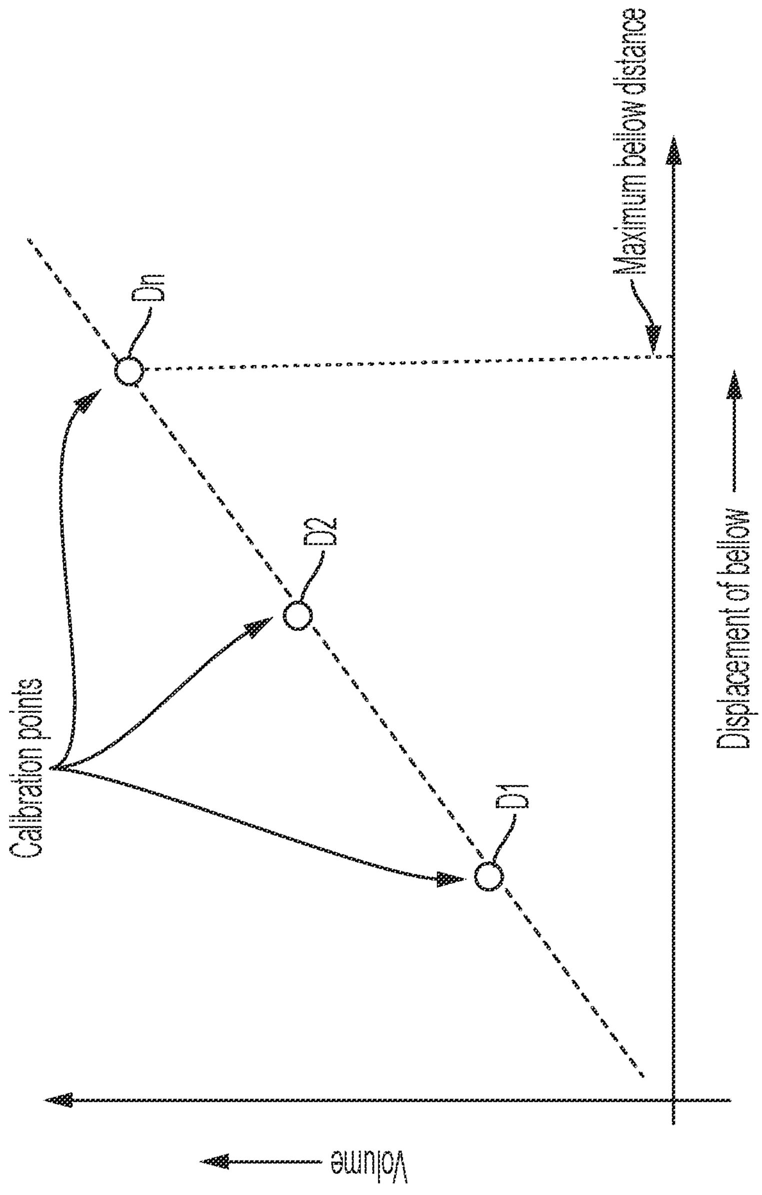

FIG. 14 illustrates that control unit 50 repeats the above procedure until a complete stroke has been mapped, noting the volume of fluid displaced over each segment D1, D2 . . . Dn of bellows 101, 102 travel. Control unit 50 sums the different volumes of fluids displaced so that it is known precisely for the particular bellows how much fluid is pumped over a first, second, third, etc., portion of a stroke, and over the entire total stroke. The above-described calibration procedure is accurate for pumping either fresh or used dialysis fluid and may be performed before treatment begins and if needed during each patient dwell until disposable set 100 is discarded at the end of treatment. To this end, it should be noted that the calibration routine of FIGS. 10 to 14 adds no additional disposable components to the version of system 10 described in connection with FIGS. 9A and 9B.

It should also be appreciated that the calibration procedure described in connection with FIGS. 10 to 14 may be used with any type of pump, such as a bellows, peristaltic, membrane or syringe pump to pump any desired fluid, such as peritoneal or hemodialysis dialysis fluid, blood, replacement fluid, heparin, citrate, an intravenous drug, saline, lactated ringers, and/or a nutritional fluid. It is contemplated to use the structure and functionality of FIGS. 10 to 14 for any type of therapy, treatment or modality, including but not limited to, plasmapherisis, hemodialysis ("HD"), hemofiltration ("HF") hemodiafiltration ("HDF"), continuous renal replacement therapy ("CRRT"), peritoneal dialysis ("PD"), intravenous drug delivery, and nutritional fluid delivery.

Incompressible Fluid

Figure 15:
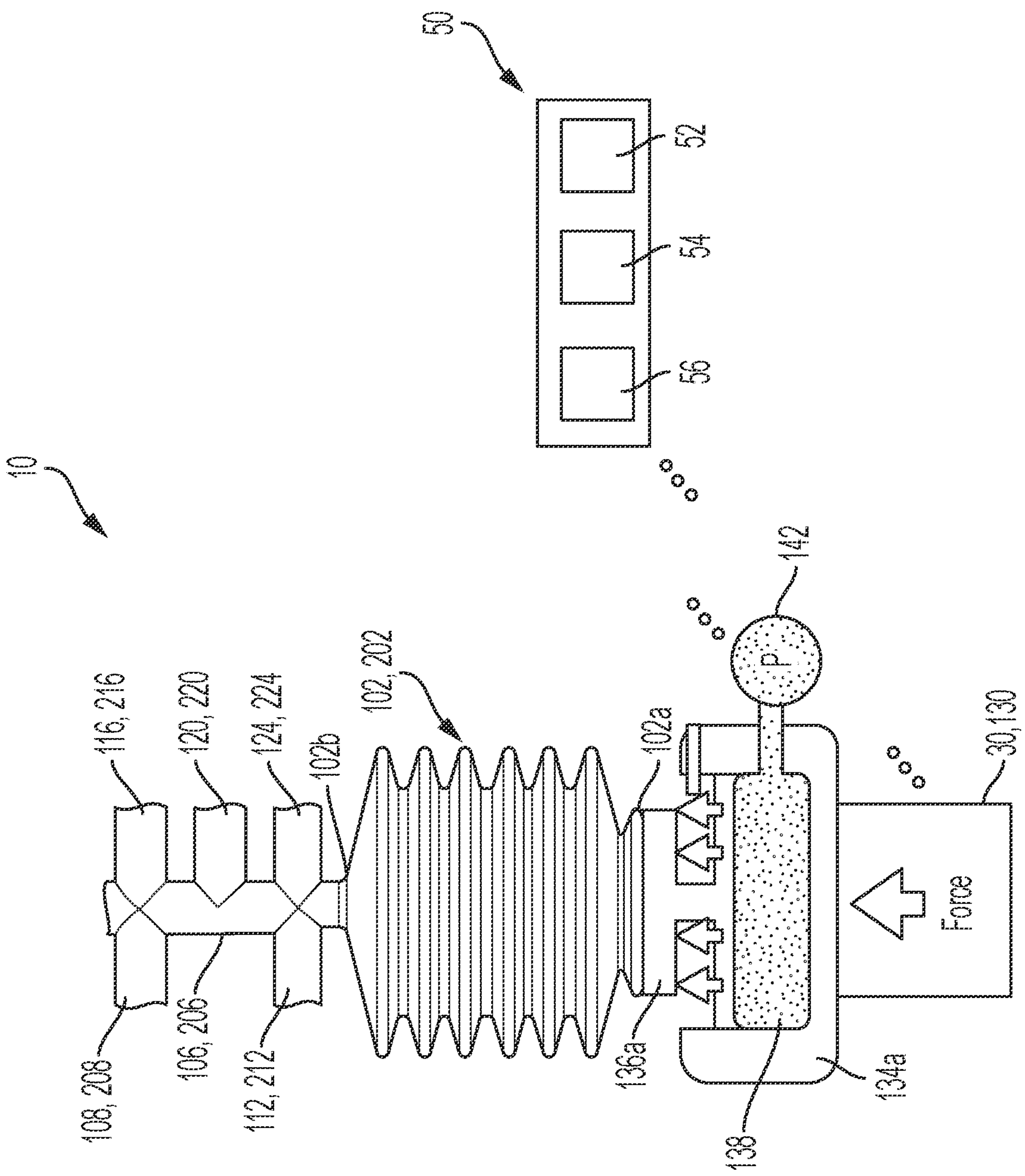
FIGS. 15 and 16 are sectioned views of different embodiments for an alternative bellows APD system of the present disclosure, which employs incompressible fluid volumes.
Figure 16:
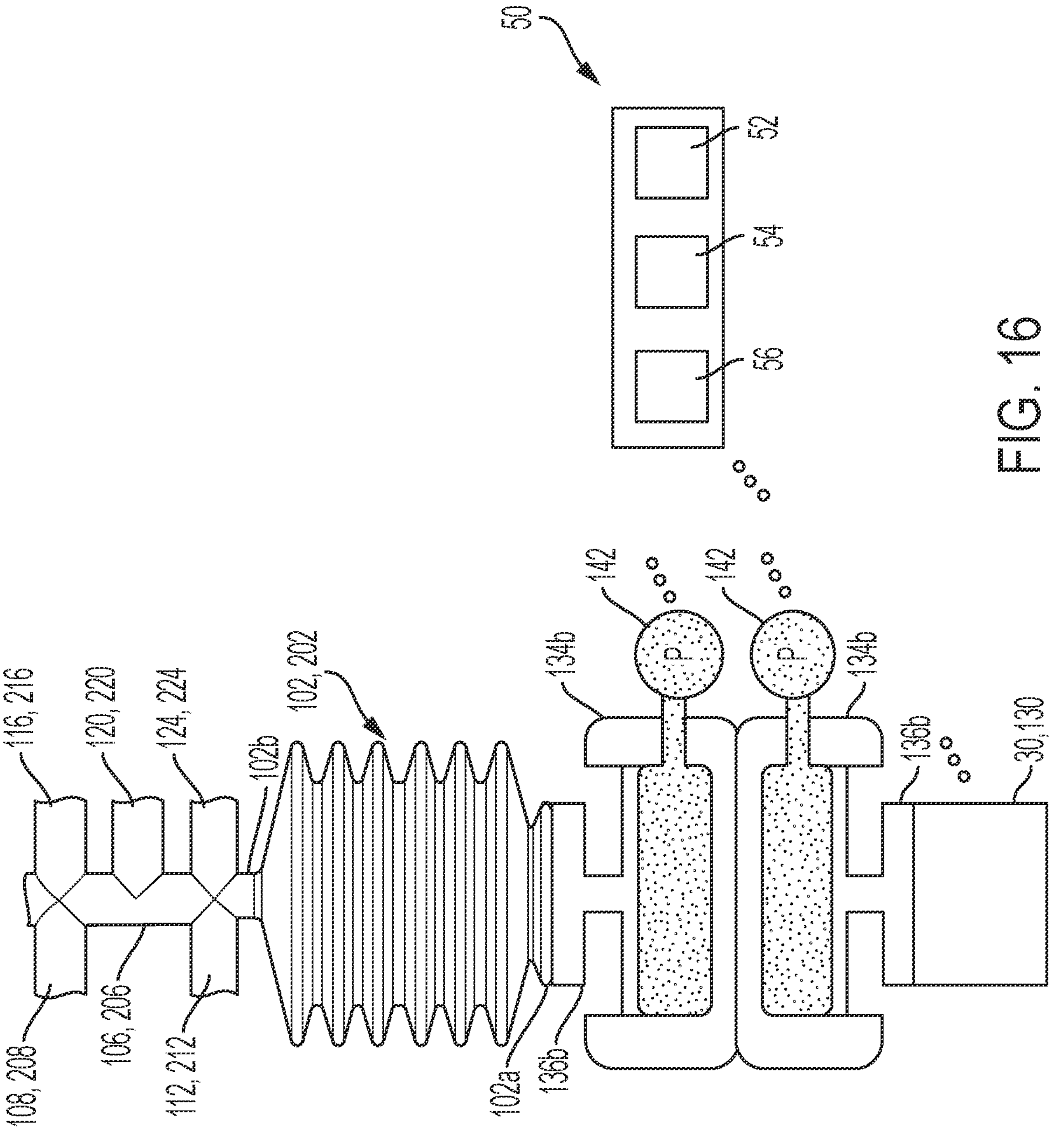

FIGS. 15 and 16 illustrate that in another version of system 10, the direct pressure of the linear actuator can be still be measured, but that the pressure pod of previous examples may be eliminated, simplifying disposable set 100 and reducing disposable cost. In FIG. 15, an incompressible fluid chamber 134*a* is provided into which a piston 136*a* is movably and in a sealed manner, e.g., via an o-ring seal, located. Chamber 134*a* and piston 136*a* capture an incompressible fluid 138, such as water or oil. Chamber 134*a* includes a fluid sensing line 140 that leads to a liquid or fluid pressure sensor 142, which outputs to control unit 50.

Any of linear actuators 30, 130 under control of control unit 50, including any of the structure and alternatives described herein, e.g., stepper motor and lead or ball screw, rack and pinion, or rotating nut motor, may be provided and operate with any kind of motion detection equipment, such as a potentiometer or encoder, outputting to control unit 50. Linear actuator 30, 130 is positioned as illustrated to advance or retract chamber 134*a* and thus may be coupled directly or indirectly to the chamber. Piston 136*a* is likewise coupled directly or indirectly to moving end 102*a* of bellows 102. Piston 136*a*, sealed inside chamber 134*a* via an o-ring, does not dislodge from chamber 134*a* when the chamber is retracted due to the fact that fluid 138 is incompressible. With an incompressible fluid, any pressure, positive or negative, may be generated without any significant change in volume. Without change in volume, piston 136*a* does not move.

In an embodiment, the inner diameter of chamber 134*a* is the same as the effective pumping diameter within bellows 102, 202 such that the pressure that linear actuator 30, 130 applies to incompressible fluid 138 is the same pressure that bellows 102, 202 applies to fresh or used dialysis fluid. This phenomenon is true for the positive pumping of fresh dialysis fluid to the patient and the removal used dialysis fluid from the patient under negative pressure. It is accordingly contemplated for control unit 50 to use the output of liquid or fluid pressure sensor 142 in a feedback loop, similar to the feedback loop of FIG. 5, to control the actual pressure of incompressible fluid 138 and dialysis fluid so as to match that of a commanded pressure stored in control unit 50.

System 10 of FIG. 16 operates in the same manner as system 10 of FIG. 15. In FIG. 16, an alternative incompressible fluid chamber 134*b* and an alternative set of pistons 136*b* are provided to hold two columns of incompressible fluid 138. Pistons 136*b* are moveable in a sealed manner, e.g., via o-ring seals, inside fluid chamber 134*b*. Each column of incompressible fluid 138 communicates via an incompressible fluid sensing line 140 with a fluid pressure sensor 142, which outputs to control unit 50. Pressure sensors 142 provide redundant readings, which are checked against each other to ensure accurate feedback to control unit 50. In an embodiment, if the pressure readouts do not match, then an alarm or alert is provided via user interface 58 and treatment is paused or terminated.

As with system 10 of FIG. 15, in system 10 of FIG. 16 the inner diameter of chamber 134*b* for both fluid columns is the same as the effective pumping diameter within bellows 102, 202, so that the pressure that linear actuator 30, 130 applies to incompressible fluid 138 in both columns is the same pressure that bellows 102, 202 applies to fresh or used dialysis fluid. Control unit 50 uses the output of fluid pressure sensors 142 (e.g., averaged or otherwise combined, or only a single pressure signal is used as feedback wherein the other pressure signal is only for checking) in a feedback loop, similar to the feedback loop of FIG. 5, to control the actual pressure of incompressible fluid 138 and dialysis fluid, so as to match that of a commanded pressure stored in the control unit.

Valve and Air Integrity

Figure 17:
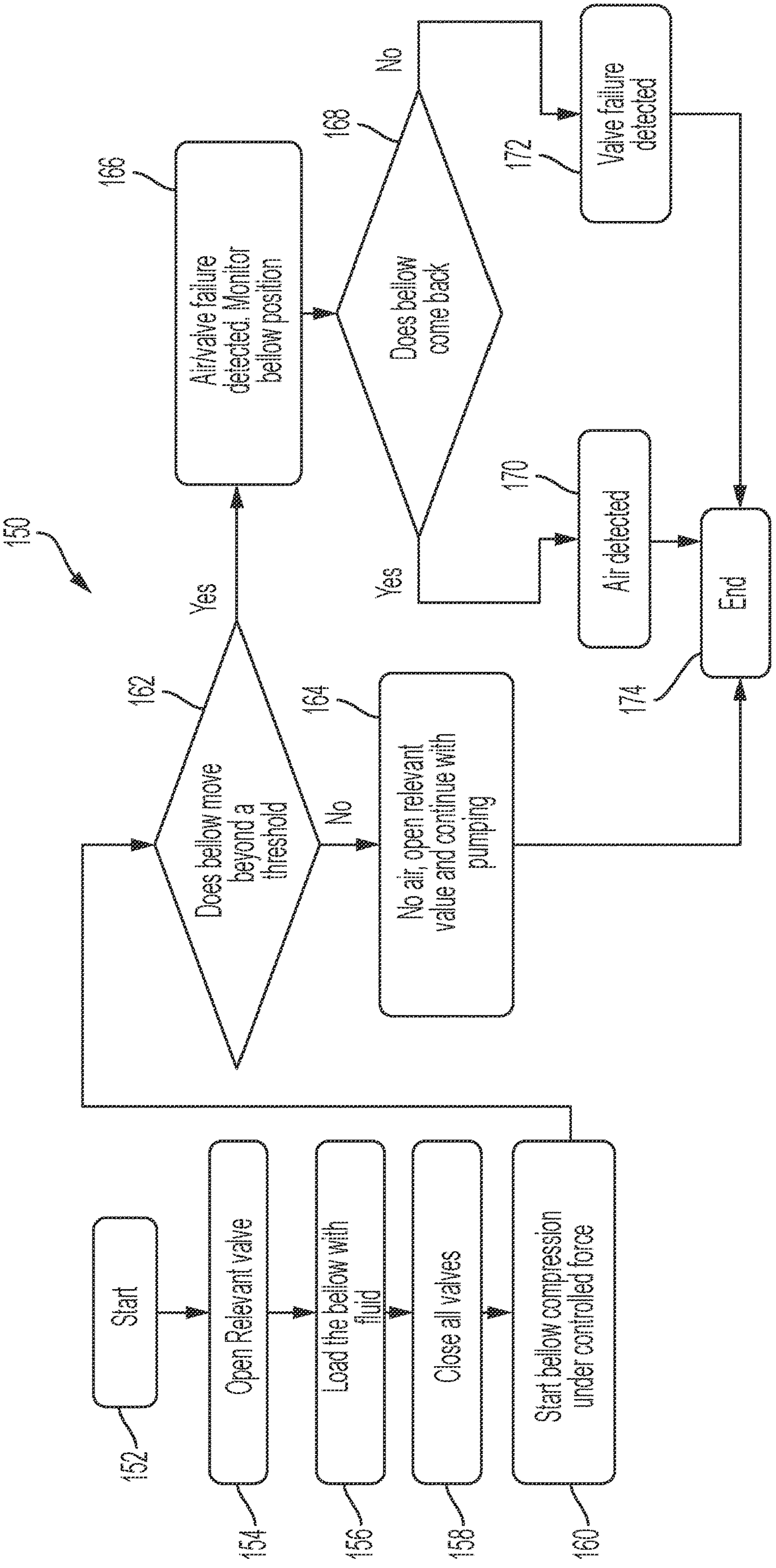
FIG. 17 is a schematic flowchart illustrating one embodiment for an air detection and valve failure detection scheme for a bellows automated peritoneal dialysis ("APD") system of the present disclosure.

FIG. 17 illustrates one embodiment of a method 150 carried out by any version of control unit 50 discussed herein for detection of (i) a failure of any of valves 44*a* to 44*e*, 44*v*, 144*a* to 144*e*, and (ii) for air detection. FIG. 17 is applicable to any bellows APD cycler and associated system discussed herein. At block 152, method 150 begins. At block 154, the valve to be interrogated is opened. At block 156, bellows 102, 202 is loaded with fluid. At block 158, all valves are closed. At block 160, compression of bellows 102, 202 occurs under a controlled force via control unit 50. At diamond 162, it is determined via potentiometer 40 (or encoder) if bellows 102, 202 moves beyond a threshold set in control unit 50. If not, as determined at block 164, then no air is present and the relevant valve may be opened to continue pumping. If so, as determined at block 166, then an air/valve failure is detected and the position of bellows 102, 202 is monitored further. At diamond 168, it is determined via potentiometer 40 (or encoder) if bellows 102, 202 moves back. If so, as determined at block 170, then control unit 50 determines air to be present. If not, as determined at block 172, then control unit 50 determines the relevant valve to have failed. A suitable response is taken by control unit 50 (e.g., halt treatment) and an error message/alarm may be provided by user interface 58. At block 174, method 150 ends.

It should be understood that various changes and modifications to the presently preferred embodiments described herein will be apparent to those skilled in the art. For example, while tubing pinch valves are illustrated, cassette based valves may be provided instead. It is therefore intended that such changes and modifications be covered by the appended claims.

The invention is claimed as follows:

1. A peritoneal dialysis system comprising:

a bellows;

a common inlet/outlet fluid receptacle in fluid communication with the bellows;

a plurality of fluid lines in fluid communication with the common inlet/outlet fluid receptacle;

a linear actuator positioned and arranged to expand and compress the bellows;

a plurality of valves positioned and arranged to allow or occlude flow through the plurality of fluid lines to or from the bellows; and a control unit configured to control the linear actuator and the plurality of valves.

2. The peritoneal dialysis system of claim 1, which includes at least one means for limiting a pressure of fluid pulled into or pushed out of the bellows.

3. The peritoneal dialysis system of claim 1, wherein the plurality of fluid lines includes at least one of a fresh dialysis fluid line, a heater line, a patient line or a drain line.

4. The peritoneal dialysis system of claim 3, which includes at least one of a fresh dialysis fluid container in fluid communication with the fresh dialysis fluid line, a heating container in fluid communication with the heater line, or a drain container in fluid communication with the drain line.

5. The peritoneal dialysis system of claim 1, wherein the common inlet/outlet fluid receptacle includes a common inlet/outlet fluid line or a pressure pod.

6. The peritoneal dialysis system of claim 1, wherein the linear actuator includes a motor in operable communication with a rack and pinion, the rack positioned and arranged to expand and compress the bellows.

7. The peritoneal dialysis system of claim 6, which includes a positional feedback device outputting to the control unit to enable the control unit to determine a current position of the bellows.

8. The peritoneal dialysis system of claim 7, wherein the positional feedback device includes a potentiometer or a motor encoder.

9. The peritoneal dialysis system of claim 7, wherein the control unit is configured to use the current position of the bellows to determine at least one of (i) a volume of fluid moved into or out of the bellows or (ii) a flowrate of fluid moved into or out of the bellows.

10. The peritoneal dialysis system of claim 1, wherein the control unit is configured to perform a priming sequence in which fluid is pulled through a first one of the fluid lines when the bellows is expanded and air is pushed out a second one of the fluid lines when the bellows is compressed.

11. The peritoneal dialysis system of claim 1, wherein the bellows is a first bellows, and which includes a second bellows positioned and arranged such that the first bellows is expanded while the second bellows is compressed and the first bellows is compressed while the second bellows is expanded.

12. The peritoneal dialysis system of claim 11, wherein the linear actuator is positioned and arranged to expand and compress the first and second bellows.

13. The peritoneal dialysis system of claim 11, wherein the common inlet/outlet fluid receptacle is a first common inlet/outlet fluid receptacle and which includes a second common inlet/outlet fluid receptacle in fluid communication with the second bellows.

14. A peritoneal dialysis system comprising:

a bellows;

a plurality of fluid lines in fluid communication with the bellows;

a plurality of valves positioned and arranged to allow or occlude flow through the plurality of fluid lines to or from the bellows;

a linear actuator positioned and arranged to expand and compress the bellows, the linear actuator including a motor; and a control unit configured to control the motor of the linear actuator and the plurality of valves, wherein (i) the motor is selected so as to be incapable of causing fluid moved by the linear actuator to exceed a pressure limit or (ii) the control unit is configured to control the motor to ensure that fluid moved by the linear actuator is within the pressure limit.

15. The peritoneal dialysis system of claim 14, wherein control of the linear actuator is based on a mathematical relationship involving the linear actuator and the motor.

16. A peritoneal dialysis system comprising:

a bellows;

a linear actuator positioned and arranged to expand and compress the bellows;

a force sensor in operable communication with the bellows and the linear actuator; and a control unit configured to control the linear actuator based on an output from the force sensor to ensure that fluid moved by the bellows is within a pressure limit.

17. The peritoneal dialysis system of claim 16, wherein control of the linear actuator is based on a maximum allowable force determined knowing the pressure limit and at least one geometrical dimension associated with the bellows.

18. The peritoneal dialysis system of claim 16, wherein the force sensor is located at a contact point between the bellows and the linear actuator.

19. A peritoneal dialysis system comprising:

a bellows;

a linear actuator positioned and arranged to expand and compress the bellows;

a pressure sensor in fluid communication with the bellows; and a control unit configured to control the linear actuator based on an output from the pressure sensor to ensure that fluid moved by the bellows is within a pressure limit.

20. The peritoneal dialysis system of claim 19, wherein the pressure sensor includes a diaphragm separating a first side of the pressure sensor in fluid communication with the bellows from a second side in operable communication with a pressure transducer.

21. The peritoneal dialysis system of claim 20, wherein the control unit is further configured to (i) cause the diaphragm to be moved to a starting position, (ii) actuate the linear actuator to cause the bellows to pump over a full range of positive and negative pressures and determine if the diaphragm flexes over the full range, (iii) if the diaphragm flexes over the full range, use the starting position for the diaphragm for treatment, and (iv) if the diaphragm does not flex over the full range, repeat (i) to (iv) moving the diaphragm to a different starting position.

22. The peritoneal dialysis system of claim 20, wherein the diaphragm is part of a tube in fluid communication with the bellows.

23. A peritoneal dialysis system comprising:

a bellows;

a piston in mechanical communication with the bellows;

a chamber, the piston in moveably sealed communication with the chamber, the chamber and the piston holding an incompressible fluid;

a pressure sensor in operable communication with the incompressible fluid; and a linear actuator positioned and arranged to move the chamber and the bellows; and a control unit configured to use feedback from the pressure sensor to attempt to control the linear actuator so that a pressure of a fluid delivered or removed by the bellows meets a commanded pressure.

24. The peritoneal dialysis system of claim 23, wherein the chamber holds a plurality of incompressible fluid columns in fluid communication with at least one pressure sensor.

* * * * *